US009804103B2

(12) United States Patent
Tsuchiya et al.

(10) Patent No.: US 9,804,103 B2
(45) Date of Patent: Oct. 31, 2017

(54) INSPECTION METHOD, TEMPLATE SUBSTRATE, AND FOCUS OFFSET METHOD

(71) Applicant: NuFlare Technology, Inc., Yokohama (JP)

(72) Inventors: Hideo Tsuchiya, Tokyo (JP); Riki Ogawa, Kanagawa (JP)

(73) Assignee: Nuflare Technology, Inc., Yokohama (JP)

( * ) Notice: Subject to any disclaimer, the term of this patent is extended or adjusted under 35 U.S.C. 154(b) by 225 days.

(21) Appl. No.: 14/710,779

(22) Filed: May 13, 2015

(65) Prior Publication Data

US 2015/0332452 A1 Nov. 19, 2015

(30) Foreign Application Priority Data

May 14, 2014 (JP) .................................. 2014-100766
Apr. 1, 2015 (JP) .................................. 2015-075454

(51) Int. Cl.
*G01N 21/00* (2006.01)
*G01N 21/956* (2006.01)
(Continued)

(52) U.S. Cl.
CPC ....... *G01N 21/956* (2013.01); *G01N 21/9501* (2013.01); *G06T 3/60* (2013.01);
(Continued)

(58) Field of Classification Search
CPC .... G01N 21/956; G01N 21/9501; G06T 3/60; G06T 7/0004; G06T 7/0008;
(Continued)

(56) References Cited

U.S. PATENT DOCUMENTS 6,048,649 A * 4/2000 Burke ................ G03F 1/44
430/324
6,151,102 A * 11/2000 Nishi ............... G03F 7/70358
250/584

(Continued)

FOREIGN PATENT DOCUMENTS

JP 2001-208697 A 8/2001
JP 2002-221495 A 8/2002
(Continued)

OTHER PUBLICATIONS

Office Action dated Jun. 29, 2017 in U.S. Appl. No. 14/153,199.

*Primary Examiner* — Hina F Ayub
(74) *Attorney, Agent, or Firm* — Oblon, McClelland, Maier & Neustadt, L.L.P.

(57) ABSTRACT

A substrate to be inspected includes a first pattern constructed with a repetitive pattern that is not resolved by a wavelength of a light source, and at least one alignment mark that is arranged on the same plane as the first pattern. The alignment mark includes a second pattern constructed with a repetitive pattern that is not resolved by the wavelength of the light source, and a programmed defect that is provided in the second pattern and not resolved by the wavelength of the light source. A focus offset is adjusted such that the strongest signal of the programmed defect is obtained with respect to a base value of a gradation value in an optical image of the programmed defect by capturing the optical image while changing a focal distance between the surface in which the first pattern is provided and an optical system.

13 Claims, 27 Drawing Sheets

(51) Int. Cl.
  *G06T 7/00* (2017.01)
  *G06T 3/60* (2006.01)
  *G01N 21/95* (2006.01)

(52) U.S. Cl.
  CPC .......... *G06T 7/0004* (2013.01); *G06T 7/0008* (2013.01); *G06T 2200/24* (2013.01); *G06T 2207/10004* (2013.01); *G06T 2207/10056* (2013.01); *G06T 2207/10148* (2013.01); *G06T 2207/30144* (2013.01); *G06T 2207/30148* (2013.01); *G06T 2207/30204* (2013.01)

(58) Field of Classification Search
  CPC ....... G06T 2200/24; G06T 2207/10004; G06T 2207/10056; G06T 2207/10148; G06T 2207/30144; G06T 2207/30148; G06T 2207/30204
  USPC .......................................... 356/237
  See application file for complete search history.

(56) References Cited

U.S. PATENT DOCUMENTS

| | | |
|---|---|---|
| 6,539,106 B1 | 3/2003 | Gallarda et al. |
| 6,690,469 B1 | 2/2004 | Shibata et al. |
| 2004/0021866 A1 | 2/2004 | Watts et al. |
| 2004/0028267 A1 | 2/2004 | Shoham et al. |
| 2004/0125375 A1 | 7/2004 | Some |
| 2004/0223141 A1 | 11/2004 | Rosengaus |
| 2006/0244976 A1 | 11/2006 | Baer et al. |
| 2007/0002344 A1 | 1/2007 | Klassen |
| 2009/0026657 A1 | 1/2009 | Nimmakayala et al. |
| 2011/0085723 A1* | 4/2011 | Badger ............ G01N 21/95607 382/144 |
| 2011/0133066 A1* | 6/2011 | Nozoe ................... H01J 37/265 250/252.1 |
| 2011/0249112 A1 | 10/2011 | Endo |
| 2011/0255770 A1 | 10/2011 | Touya et al. |
| 2012/0274931 A1 | 11/2012 | Otani et al. |
| 2013/0141723 A1* | 6/2013 | Wei ....................... G03F 9/7046 356/400 |
| 2013/0176559 A1 | 7/2013 | Ogawa et al. |
| 2014/0002826 A1 | 1/2014 | Inoue et al. |
| 2014/0043467 A1 | 2/2014 | Yamashita |
| 2014/0055774 A1 | 2/2014 | Sugihara et al. |
| 2014/0055780 A1 | 2/2014 | Ogawa et al. |
| 2014/0072202 A1 | 3/2014 | Ogawa et al. |
| 2014/0104412 A1 | 4/2014 | Inoue et al. |
| 2014/0111636 A1 | 4/2014 | Inoue et al. |
| 2014/0190006 A1* | 7/2014 | Setomoto ................ H01J 37/12 29/852 |
| 2014/0204202 A1 | 7/2014 | Ogawa et al. |
| 2014/0232032 A1* | 8/2014 | Yoshikawa ........... G03F 7/0002 264/40.1 |
| 2014/0232849 A1 | 8/2014 | Ogawa et al. |
| 2015/0054941 A1 | 2/2015 | Ogawa |

FOREIGN PATENT DOCUMENTS

| | | |
|---|---|---|
| JP | 2006-47308 A | 2/2006 |
| JP | 2006-512588 A | 4/2006 |
| JP | 2006-516065 | 6/2006 |
| JP | 2007-225341 A | 9/2007 |
| JP | 4236825 B2 | 3/2009 |
| JP | 2009-192520 A | 8/2009 |
| JP | 2010-534406 | 11/2010 |
| JP | 2012-026977 | 2/2012 |
| JP | 2012-127856 A | 7/2012 |
| JP | 2012-185178 A | 9/2012 |
| JP | 2014-137358 A | 7/2014 |
| WO | WO 2010/050488 A1 | 5/2010 |

* cited by examiner

INSPECTION METHOD, TEMPLATE SUBSTRATE, AND FOCUS OFFSET METHOD

CROSS-REFERENCE TO THE RELATED APPLICATION

The entire disclosure of the Japanese Patent Application No. 2014-100766 filed on May 14, 2014 and 2015-075454 filed on Apr. 1, 2015, including specifications, claims, drawings, and summaries, on which the Convention priority of the present application is based, are incorporated herein in their entirety.

FIELD OF THE INVENTION

The present invention relates to an inspection method, a template substrate, and a focus offset method.

Recently, with an increasing integration degree of a semiconductor device, the dimensions of individual elements have become finer, and the widths of wiring and gate constituting each element have also become finer.

EUV (Extreme Ultraviolet) lithography and nanoimprint lithography (NIL) have attracted attention as technologies for forming fine patterns on a semiconductor wafer. Since the EUV lithography uses extreme ultraviolet light as a light source to transfer patterns of EUV mask onto the wafer, it is possible to form finer patterns on the wafer than a conventional exposure apparatus using ArF light. In the nanoimprint lithography, a fine pattern is formed in a resist by pressuring a template having a nanometer-scale fine structure to the resist on the wafer. In both the EUV lithography and the nanoimprint lithography, a pattern formed in the EUV mask and the template being an original plate is finer when compared with conventional ArF lithography. Thus, high inspection accuracy is required for the inspection thereof.

An exposure apparatus called a stepper or a scanner is used in the transfer process in the EUV lithography. In the exposure apparatus, light is used as a transfer light source, and a circuit pattern on the mask is projected onto the wafer while reduced from about one-fourth to about one-fifth size. Accordingly, the dimension of a circuit pattern to be formed in the mask is about four times to about five times as large as a dimension of a circuit pattern on the wafer. On the other hand, in a template used in the nanoimprint lithography, a circuit pattern having the same dimension as a circuit is formed by digging a printing plate down to a predetermined depth. In a contemporary semiconductor device, a line width of a pattern or a width of a space between patterns might be from ten nanometers to several tens of nanometers, and a depth of a dugout portion might be from several tens of nanometers to one hundred nanometers.

Because the template pattern has the dimension identical to the dimension of the circuit, the defect existing in the template has a larger influence on the pattern imprinted to the wafer compared with the mask pattern. Because the template is used in the imprint a plurality of times, the defect is wholly imprinted to the wafer together with the pattern. Accordingly, in inspecting the template pattern, higher accuracy is required compared with the inspection of the mask pattern. For example, JP 2012-26977 A discloses an inspection apparatus that detects the defect of the template.

The pattern formed in the template cannot be resolved when the pattern is finer than a wavelength of the light source in the inspection apparatus. Generally the limit dimension of the pattern is known as a Rayleigh resolution limit. Nowadays, with the progress of fine circuit patterns, it is possible that the dimension of the pattern becomes finer than the resolution of the optical system in the inspection apparatus.

Assuming that NA is a numerical aperture of the optical system in the inspection apparatus and that $\lambda$ is a wavelength of the light source, the resolution of the optical system is expressed by the equation (1). The numerical aperture NA is usually in the range of approximately 0.7 to approximately 0.8; $k1$ is a coefficient depending on an image forming condition, and is in the range of approximately 0.5 to approximately 1.

$$R = k_1 \frac{\lambda}{NA} \qquad (1)$$

In a contemporary semiconductor device manufacturing process, in inspecting the mask used in reduced projection exposure of the circuit pattern to the wafer, the mask is irradiated with continuous light having a wavelength of approximately 200 nm close to the wavelength of the light source of the exposure apparatus. The light transmitted through or reflected by the mask is received by a sensor through a proper magnification optical system to obtain an electrical signal constituting an optical image of the mask. The dimension of the pattern formed in the mask is approximately four times as large as the line width (several tens of nanometers) of the pattern to be formed on the wafer, namely, approximately one hundred nanometers to several hundred nanometers.

In the equation (1), when the wavelength of the light source is set to 200 nm, and when the numerical aperture is set to 0.7, an equation (2) is obtained.

$$R = 0.5 \times \frac{200}{0.7} = 143 (nm) \qquad (2)$$

According to an equation (2), the resolution limit size is 143 nm in this case. That is, when the patterns of the mask come closer than 143 nm to each other, an electrical signal of a brightness amplitude corresponding to the pattern is not obtained by the sensor. This is similar for a pattern of a template. Because the pattern of the template has the same dimension as the circuit to be formed on the wafer, the pattern of the template cannot be resolved in principle. The shapes of some of the non-repetitive, slightly thick patterns called a lead wire or a gate wire can occasionally be distinguished.

Instead of the inspection optical system provided with the above-mentioned light source, a method for acquiring a pattern by applying an electron beam or an atomic force is conceivable as a method for resolving the fine pattern to identify the defect. However, for the inspection in which the electron beam or the atomic force is used, there is a problem in that the inspection is not suitable for mass production of semiconductor device because of low throughput.

In the template in which a repetitive pattern finer than the resolution of the optical system in the inspection apparatus is formed, when a reflection optical image of the template is acquired, the optical image (electrical signal image) has brightness corresponding to a film quality of the template at a location where the pattern is not arranged. For example, the optical image becomes an even brightness close to a white level determined by calibration. At a location where the pattern is arranged, the optical image has the brightness different from that at the location where the pattern is not arranged, for example, the optical image is observed as an even gray image that is between the white level and a black level in the brightness.

On the other hand, when the defect exists at the location where a predetermined pattern is periodically formed, the periodicity of the pattern is disturbed, and the optical image becomes an image in which the brightness is changed according to a degree of the defect in the even gray image. For example, the brightness change is observed as an isolated white or black point.

The defect can be detected in the pattern finer than the resolution of the optical system by detecting the brightness change caused by the disturbance of the periodicity. Specifically, in the identical template, the defect is detected by using a die-to-die comparison method in which optical images of a plurality of dies are compared to each other or a cell comparison method in which optical images in the regions where the identical pattern is formed are compared to each other. For example, the two dies, which both appear to be the even gray image when the patterns have no defects, are compared to each other to determine that the image having the brightness change caused by the disturbance of the periodicity has the defect.

When the optical image is captured while a focal position between the pattern and the optical system is changed for the repetitive pattern finer than the resolution of the optical system, the brightness change, namely, a variation in gradation value is observed in each optical image. The variation in gradation value depends on the focal position. The focal position where the variation becomes the maximum is the position where the contrast of the optical image is maximized, namely, a focusing position. However, it is well known that a signal-to-noise (S/N) ratio of the defect inspection is occasionally improved when the defect is inspected while a given distance (focus offset) is intentionally provided with respect to the focusing position. Therefore, the focusing position where the contrast of the optical image becomes the maximum is obtained, and the inspection is performed using the position where the focusing position is corrected by the focus offset as the optimum focal position.

The focus offset also has the optimum value, and the optimum value depends on a kind, a shape, and a dimension of the defect.

For example, it is considered that a line-and-space pattern is regularly arrayed with given periodicity. Assuming that the broken pattern defect is generated in the line-and-space pattern by disconnection, the defect is seen as a white bright spot in the even gray image when the defect is observed with the focus offset. At this point, when the focus offset is changed, the defect is seen as a black spot in the even gray image. In the intermediate focus offset, amplitude of a defect signal cannot be obtained by an image sensor, and therefore the defect cannot be observed.

For example, when the defect in which the adjacent line patterns are partially connected to each other to form a pattern bridge defect exists in the line-and-space pattern, the pattern bridge defect caused by the short-circuit is seen as black-and-white inversion of the broken pattern defect caused by the disconnection. That is, when the focus offset seen as the white bright spot in the broken pattern defect caused by the disconnection is applied to the pattern bridge defect caused by the short-circuit, the pattern bridge defect caused by the short-circuit is seen as the black spot while the black-and-white inversion of the broken pattern defect caused by the disconnection is generated. In the focus offset seen as the black spot in the broken pattern defect caused by the disconnection, the pattern bridge defect caused by the short-circuit is seen as the white bright spot.

In the above example, when the shape or dimension of the pattern bridge defect or broken pattern defect varies, the brightness of the defect, namely, the brightness of the white or black spot changes, or the focus offset in which the brightness becomes the maximum changes.

Therefore, in inspecting the template, the defect is detected by performing a preliminary inspection, the focus offset is adjusted using the defect, the optimum focus offset is found in order to detect the defect, and the inspection is performed. However, the focus offset cannot be adjusted when the defect is not detected in the preliminary inspection. For this reason, when the defect is not detected in the subsequent inspection, it is not distinguished whether the defect is not detected due to the actual absence of the defect or the improper focus offset, which results in a problem in that inspection quality cannot be guaranteed.

The present invention has been devised to solve the problem described above. An object of the present invention is to provide an inspection method for properly adjusting the focus offset to be able to accurately detect the defect of the pattern finer than the resolution of the optical system in the inspection apparatus.

Another object of the present invention is to provide a template substrate suitable for the inspection method for properly adjusting the focus offset to be able to accurately detect the defect of the pattern finer than the resolution of the optical system in the inspection apparatus. The template substrate may also be referred to as 'template' in the present invention.

Another object of the present invention is to provide a focus offset method suitable for the inspection method for accurately detecting the defect of the pattern finer than the resolution of the optical system in the inspection apparatus.

Other advantages and challenges of the present invention are apparent from the following description.

SUMMARY OF THE INVENTION

According to one aspect of the present invention, in an inspection method for inspecting a substrate to detect a defect using an optical image obtained by irradiating a substrate with light emitted from a light source through an optical system, and causing the light reflected by the substrate to be incident to a sensor through the optical system, the substrate includes a first pattern constructed with a repetitive pattern that is not resolved by a wavelength of the light source, and at least one alignment mark that is arranged on the same plane as the first pattern. The alignment mark includes a second pattern constructed with a repetitive pattern that is not resolved by the wavelength of the light source; and a programmed defect that is provided in the second pattern and not resolved by the wavelength of the light source. A focus offset is adjusted such that a strongest signal of the programmed defect is obtained with respect to a base value of a gradation value in an optical image of the programmed defect by capturing the optical image while changing a focal distance between the surface in which the first pattern is provided and the optical system. A defect of the first pattern is detected by capturing an optical image of the first pattern after the focus offset is adjusted.

Further to this aspect of the present invention, the programmed defect includes a plurality of defects of an identical kind and different size.

When signals of the programmed defect having the identical shape and different size change temporally depending on the size, the inspection is stopped without performing the process of detecting a defect of the first pattern by capturing an optical image of the first pattern.

Further to this aspect of the present invention, the first pattern and the second pattern are a line-and-space pattern or a rectangular pattern, and the programmed defect includes at least one of a pattern bridge defect in which lines or rectangles are short-circuited with each other and a broken pattern defect in which the line is disconnected or the rectangle is lacking.

Further to this aspect of the present invention, the substrate is a template substrate, and the alignment mark includes the second pattern, and a region, where the second pattern is not arranged but a mark used in alignment is formed by contrast with a region where the second pattern is arranged.

Further to this aspect of the present invention, the focus offset obtained from the optical image of the programmed defect provided in the second pattern, is optimized in the first pattern when the first pattern differs from the second pattern in size or when the first pattern differs from the second pattern in a duty ratio defined by a width and a pitch of each line while both the first pattern and the second pattern are a line-and-space pattern.

Further to this aspect of the present invention, the optical system includes a polarization beam splitter, a half-wavelength plate, a Faraday rotator, and an objective lens. After the focus offset is adjusted, light emitted from the light source is reflected by a polarization beamsplitter. The light is transmitted through the half-wavelength plate, the Faraday rotator, the objective lens. The substrate is irradiated by the light including a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern. The light reflected by the substrate is transmitted through the objective lens, the half-wavelength plate, the Faraday rotator, and the polarization beamsplitter. An optical image of the programmed defect is captured by causing the light to be incident to the sensor. A gradation value in each pixel with respect to the optical image of the programmed defect is obtained. (1) A rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values, is acquired. A magnetic field to the Faraday rotator is applied such that the acquired rotation angle is obtained. An optical image of the first pattern is captured while the magnetic field is applied to the Faraday rotator. A defect of the first pattern is detected by using the optical image of the first pattern. The first pattern and the second pattern are a line-and-space pattern or a rectangular pattern. The programmed defect includes at least one of a pattern bridge defect in which lines or rectangles are short-circuited each other and a broken pattern defect in which the line is disconnected or the rectangle is lacking.

The rotation angle obtained from the optical image of the programmed defect provided in the second pattern, is optimized in the first pattern when the first pattern differs from the second pattern in size or when the first pattern differs from the second pattern in a duty ratio defined by a width and a pitch of each line while both the first pattern and the second pattern are the line-and-space pattern.

The substrate is a template substrate, and the alignment mark includes the second pattern, and a region, where the second pattern is not arranged but a mark used in alignment is formed by contrast with a region where the second pattern is arranged.

When signals of the programmed defect including a plurality of defects having an identical kind and different size, change temporally depending on the size, the inspection is stopped without performing the process of detecting a defect of the first pattern by capturing an optical image of the first pattern.

Further to this aspect of the present invention, the substrate includes the alignment mark in a scribe region that is arranged at an outer periphery of a region where the first pattern is provided.

The alignment marks are arranged in four corners of the substrate.

According to another aspect of the present invention, a template substrate comprises a first pattern constructed with a repetitive pattern that is not resolved by a wavelength of the light source, and at least one alignment mark that is arranged on the same plane as the first pattern. The alignment mark includes a second pattern constructed with a repetitive pattern that is not resolved by the wavelength of the light source, and a programmed defect that is provided in the second pattern and not resolved by the wavelength of the light source. The alignment mark includes the second pattern, and a region, where the second pattern is not arranged but a mark used in alignment is formed by contrast with a region where the second pattern is arranged.

According to another aspect of the present invention, in a focus offset method in an inspection method for inspecting a substrate to detect a defect using an optical image obtained by irradiating a substrate with light emitted from a light source through an optical system, and causing the light reflected by the substrate to be incident to a sensor through the optical system, the substrate includes a first pattern constructed with a repetitive pattern that is not resolved by a wavelength of the light source, and at least one alignment mark that is arranged on the same plane as the first pattern. The alignment mark includes a second pattern constructed with a repetitive pattern that is not resolved by the wavelength of the light source, and a programmed defect that is provided in the second pattern and not resolved by the wavelength of the light source. A focus offset is adjusted such that a strongest signal of the programmed defect is obtained with respect to a base value of a gradation value in an optical image of the programmed defect by capturing the optical image while changing a focal distance between the surface in which the first pattern is provided and the optical system.

DETAILED DESCRIPTION OF THE EMBODIMENT

First Embodiment

Figure 2:
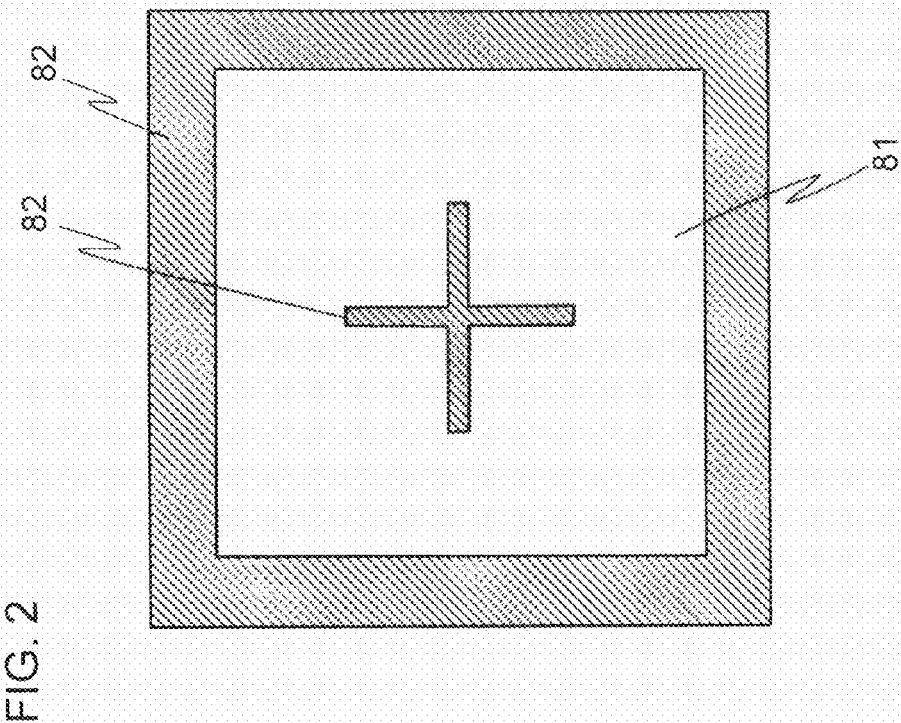
FIG. 2 is an enlarged plan view of a portion of the alignment mark of the mask.

As described above, in inspecting the template in which a repetitive pattern finer than the resolution of the optical system is formed, the appropriate defect is detected by performing the preliminary inspection, the focus offset is adjusted using the defect, and the inspection is performed after the focus offset optimum for detecting the defect is found out. However, the focus offset cannot be adjusted in the case that the defect is not detected by the preliminary inspection. When the defect is not detected in the subsequent inspection, it is not understood whether the defect is not detected due to the actual absence of the defect or the improper focus offset.

In a first embodiment, a programmed defect is previously formed in the template, and the focus offset is adjusted using the programmed defect. Specifically, the programmed defect is provided in an imprint surface of the template. In the first embodiment, the programmed defect is formed in an alignment mark provided in the imprint surface. The alignment mark includes a cross or L-shape mark, and a repetitive pattern that is visible as a gray tone around the cross or L-shape mark. The programmed defect is formed in a part of the repetitive pattern. In the alignment mark, a portion that has the appearance of a cross or L-shape mark is a matrix portion in which the pattern is not formed. On the other hand, a portion other than the portion that has the appearance of a cross or L-shape mark is defined as a "dummy fill region" in the first embodiment, and the repetitive pattern finer than the resolution limit of the optical system is formed in the dummy fill region.

Generally, the alignment mark is used in various alignments in a process of manufacturing a semiconductor integrated circuit. Different alignment marks are provided at the appropriate location of the template according to the kind of alignment required. In the alignment mark of the first embodiment arranged in the imprint surface of the template, a mark having a shape necessary for the alignment and the programmed defect are formed in the dummy fill region where the repetitive pattern finer than the resolution of the optical system is arranged in a rectangular region having a proper dimension, and the mark and the programmed defect are also used to adjust the focus offset. At this point, there is no limitation to the kind of alignment in which the alignment mark is originally used. That is, in the alignment mark of the first embodiment, it is only necessary to form the repetitive pattern finer than the resolution of the optical system and the programmed defect, but there is no particular limitation to the shape necessary for the alignment.

The alignment in which the alignment mark is originally used will be described below. Although a mask is mainly cited as an example in the following description, the same method may also be used for the template.

For example, the alignment mark is provided for the purpose of the alignment between a wafer and a mask or the alignment between the wafer and the template. The alignment mark is also used to form multilayer interconnection of a Large Scale Integration (LSI). In an LSI manufacturing process, about ten kinds of layers are sequentially formed on a silicon wafer to make vertical and horizontal interconnections and functional cells. The masks having different patterns are used to form the layers, and the layers are superimposed on each other so as not to deviate. At this point, the alignment mark is used to align the upper layer with the lower layer. Because the alignment mark is a pattern that is not necessary for LSI operation, the alignment mark is provided outside a region where an LSI pattern is formed so as not to have an influence on the LSI pattern. In the first embodiment, particularly the alignment mark is provided in an outer peripheral portion of a pattern surface of the mask or an imprint surface of the template.

Some of the alignment marks are used in an inspection. In the inspection, for example, when the mask is placed at a predetermined position on an XYθ-table provided in an inspection apparatus, the inspection apparatus performs a correction calculation by automatically calculating a rotation angle (θ) from the predetermined position of the mask or whole extension and contraction of the pattern due to a temperature. At this point, the rotation angle or the extension and contraction are calculated using the alignment mark.

In the case that the correction calculation is performed in the inspection apparatus, a plate alignment is performed first. In the plate alignment, XY-coordinate axes of the pattern surface of the mask are aligned with parallelism and perpendicularity of a traveling axis of the XYθ-table in the inspection apparatus. Therefore, a rotation error or an extension and contraction error of the mask pattern is normalized with respect to the optical system of the inspection apparatus. For example, X-axes and Y-axes of the two alignment marks that are provided in the mask to establish a horizontal or vertical position relationship on design are adjusted so as to be parallel or perpendicular to the traveling axis of the XYθ-table, the mask is adjusted so as to be located at the predetermined position by rotating a θ-axis of the XYθ-table based on the alignment mark, and a distance between the two alignment marks is measured. An extension and contraction ratio of the mask is calculated by comparing the measured distance to a theoretical distance between the alignment marks, which is previously provided to the inspection apparatus. Accuracy of an inspection result can be enhanced by reflecting the obtained value on the correction calculation of the position or dimension of the pattern measured in the inspection process.

The alignment mark of the first embodiment includes the dummy fill region where the repetitive pattern finer than the resolution of the optical system is arranged in the rectangular region having the proper dimension, the mark (such as the cross or L-shape mark) having the shape necessary for the alignment, and the programmed defect.

Figure 1:
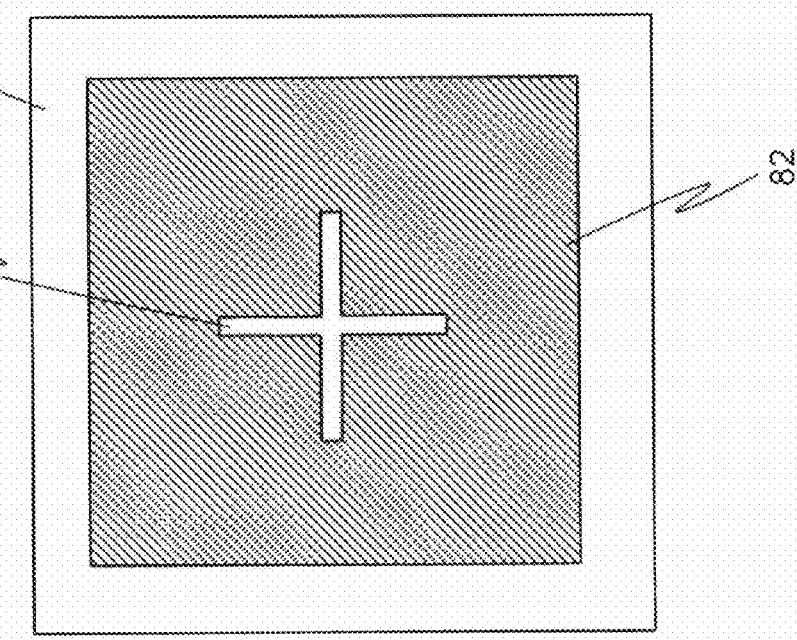
FIG. 1 is an enlarged plane view of a portion of the alignment mark of the mask.
Figure 4:
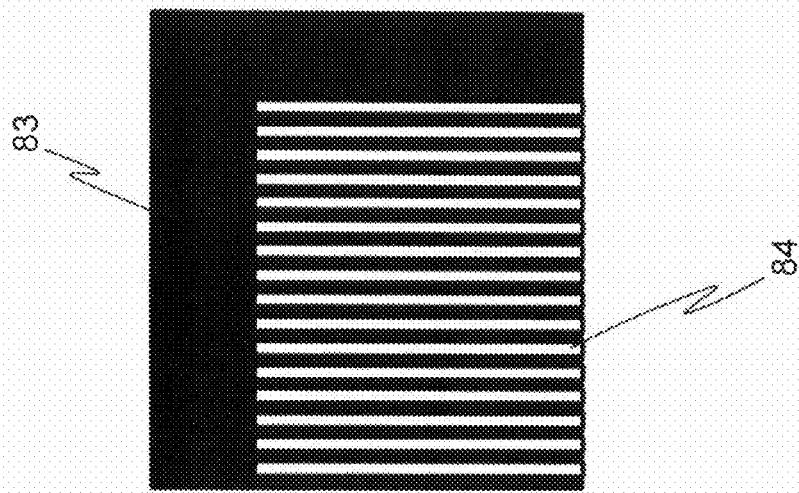
FIG. 4 is an enlarged view of the region shown in FIG. 3.
Figure 3:
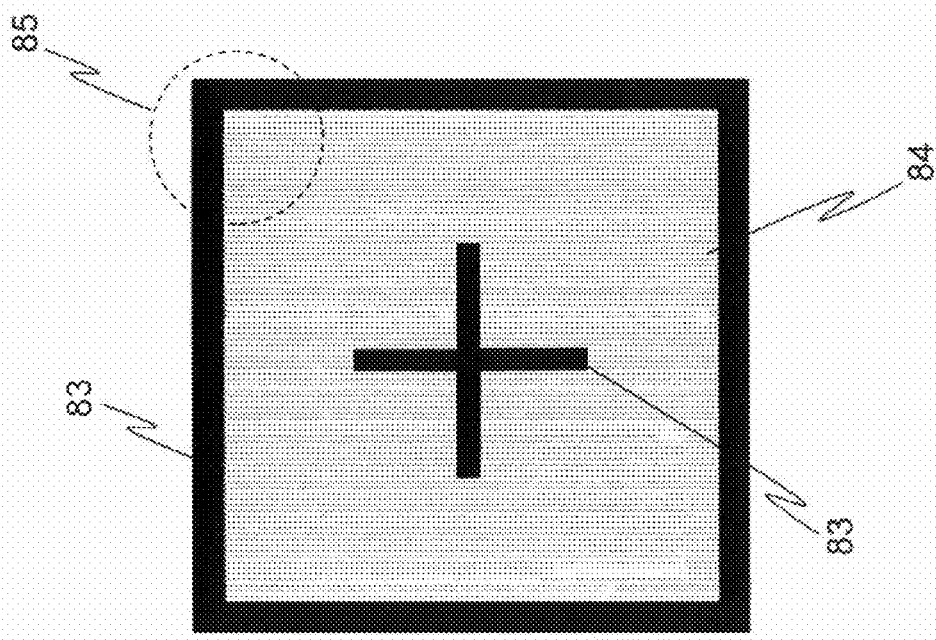
FIG. 3 illustrates an example of the alignment mark formed in the template.
Figure 5:
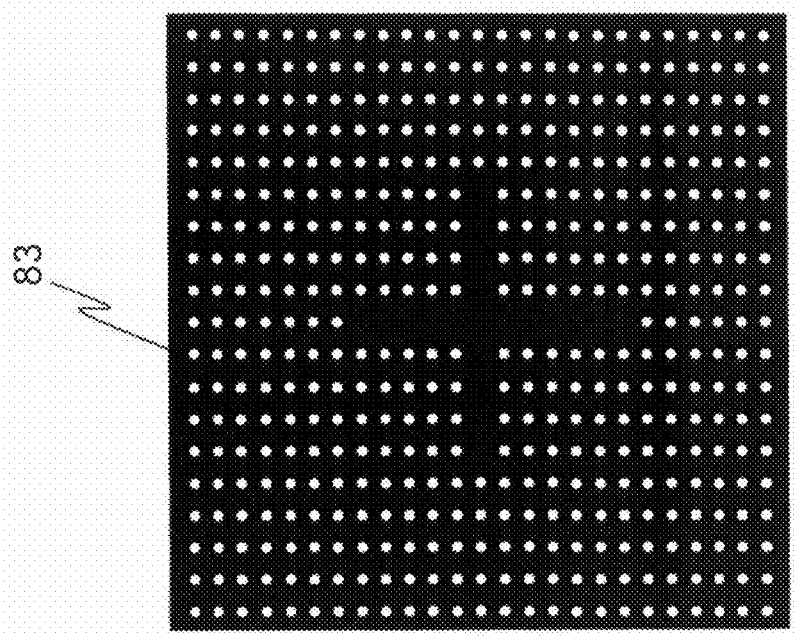
FIG. 5 illustrates another example of the alignment mark formed in the template.

FIGS. 1 and 2 illustrate an alignment mark for optical mask as a comparative example. On the other hand, FIGS. 3 to 5 illustrate an alignment mark of the first embodiment. In FIGS. 3 to 5, the programmed defect used to adjust the focus offset is omitted.

As illustrated in FIG. 1, in the alignment mark for optical mask, a square light shielding film 82 is provided on a glass substrate 81, and the cross glass substrate 81 is exposed from the light shielding film 82, which allows the matrix portion and the cross marks to be formed. Alternatively, as illustrated in FIG. 2, the square matrix portion of the glass substrate 81 is exposed from the light shielding film 82, and the cross mark can be formed in the square matrix portion by the light shielding film 82.

On the other hand, the template of the first embodiment in FIGS. 3 to 5 is one in which a circuit pattern is engraved in a glass substrate, and the template (template substrate) has a mesa structure in which a portion corresponding to an area necessary for the imprint is left in a convex shape while a surrounding area of the portion is removed by digging. The circuit pattern to be imprinted is formed in the convex portion, and the convex portion is pressed against a resist on the wafer to imprint the circuit pattern. Because of non-existence of a light shielding film, the alignment mark of the template is formed using contrast caused by existence or non-existence of the pattern. Specifically, a fine repetitive pattern that cannot be resolved by a wavelength of the light source in the inspection apparatus, the pattern having the dimension equal or similar to the pattern imprinted to the wafer, is periodically arranged, and a portion appearing to have a gradation of grey is provided. For example, line patterns having widths of several tens of nanometers or hole patterns having diameters of several tens of nanometers are arranged at intervals of several tens of nanometers. The contrast between the pattern and the portion appearing to have a matrix brightness of the template caused by the non-existence of the pattern is used. At this point, the portion appearing to have a matrix brightness of the template is used as the shape of the mark used in the alignment. For example, a cross shape, an L-shape, or a shape in which plural bars are combined can be used in the template in the same fashion as the mask. The fine pattern is also formed with use of the electron-beam lithography apparatus.

FIG. 3 illustrates an example of the alignment mark formed in the template. FIG. 4 is an enlarged view of a region 85 in FIG. 3. As illustrated in FIGS. 3 and 4, the cross mark is formed using the contrast between a region where a fine line-and-space pattern 84 is arranged and a region where a matrix 83 of the template is seen because the line-and-space pattern 84 is not arranged.

FIG. 5 illustrates another example of the alignment mark formed in the template. In another example of FIG. 5, the matrix 83 of the template is left into the cross shape while many fine hole patterns are periodically arranged. Therefore, the cross mark is formed using the contrast between the region where the hole pattern is provided and the matrix 83 of the template.

Figure 6:
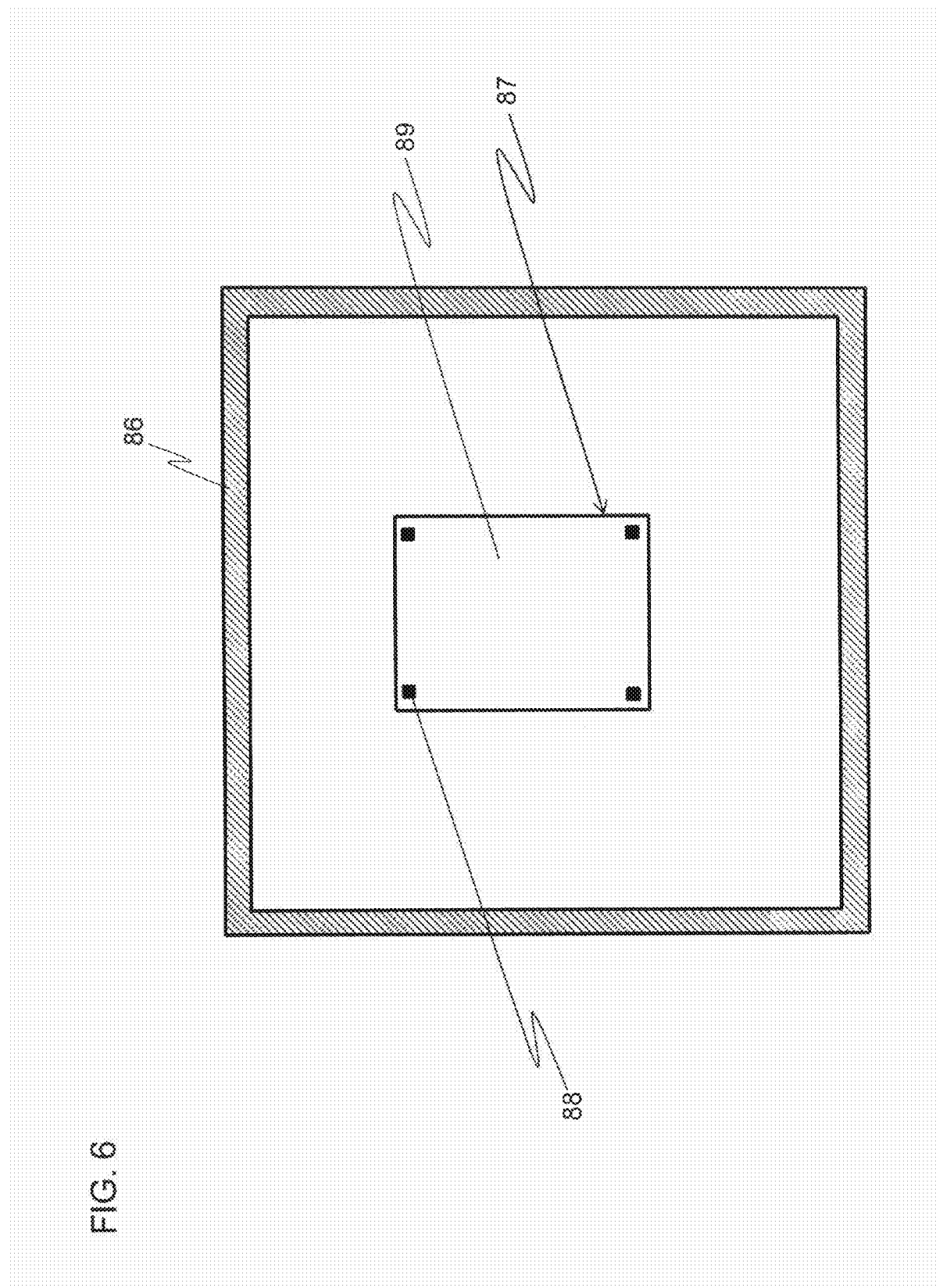
FIG. 6 is a plan view illustrating a state in which the template is arranged on a table of the inspection apparatus.

In the first embodiment, alignment marks of the template used to adjust the focus offset are arranged in regions close to four corners at an outer periphery of the convex imprint surface of the template. FIG. 6 is a plan view schematically illustrating a state in which the template is arranged on a table of the inspection apparatus. In FIG. 6, the template is designated by the numeral 87, and an imprint surface 89 is the region to be inspected. The table is designated by the numeral 86, and a portion in which the template 87 and the table 86 overlap each other is the region where the inspection is not performed. As illustrated in FIG. 6, alignment marks 88 provided in the template 87 are arranged in the four corners close to the outer periphery of an imprint surface 89 of the template 87.

Next, a programmed defect formed in an alignment mark according to the present embodiment will be described.

Figure 12:
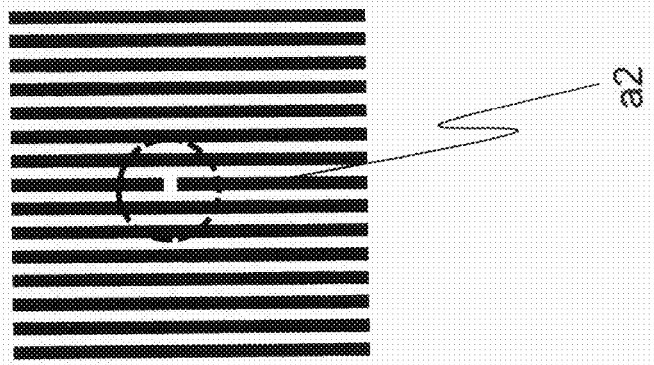
FIG. 12 illustrates an example of the broken pattern defect.
Figure 11:
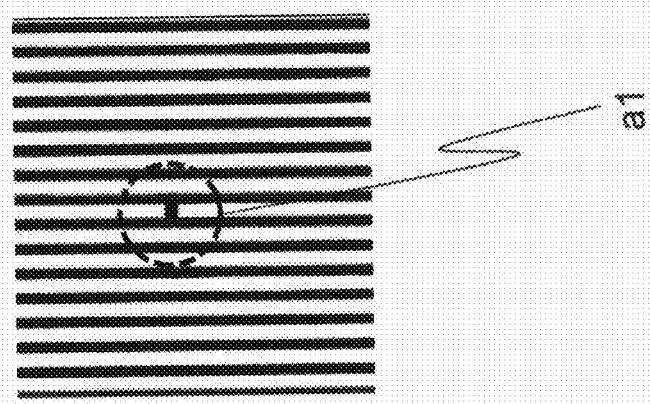
FIG. 11 illustrates an example of the pattern bridge defect.

A pattern bridge defect in which lines short-circuit each other or a broken pattern defect in which the line is disconnected is detected in the inspection of the pattern finer than the resolution limit of the optical system. FIG. 11 illustrates an example of the pattern bridge defect. In a region a1, the two adjacent lines are connected to each other to form the pattern bridge defect. FIG. 12 illustrates an example of the broken pattern defect. In a region a2, the line is partially disconnected. The pattern bridge defect and the broken pattern defect have a serious influence on performance of the template. Therefore, a programmed defect that simulates the pattern bridge defect or the broken pattern defect may be formed in the alignment mark.

Figure 7:
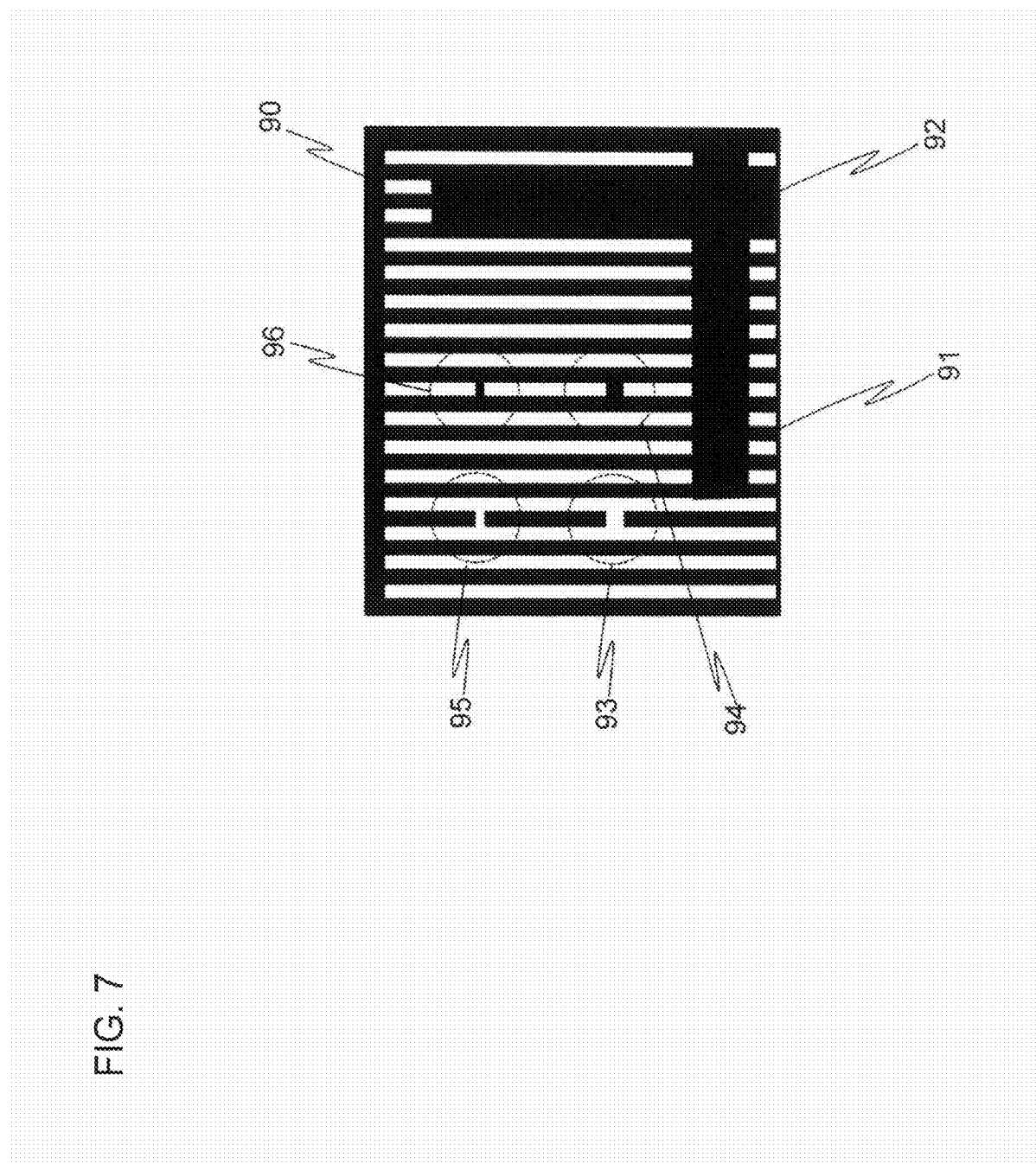
FIG. 7 is an example of an enlarged plan view of a part of the alignment mark provided in the template.

FIG. 7 is a partially enlarged plan view illustrating an example of the alignment mark provided in each of the four corners of the imprint surface of the template. The alignment mark simulates the pattern that is of an inspection target provided in the imprint surface of the template, namely, a first periodic pattern (not illustrated) to be imprinted to the wafer. The alignment mark includes a fine second pattern 91 and a region where the second pattern 91 is not arranged but a mark 92 is formed. The fine second pattern 91 has the dimension and periodicity equal to those of the first pattern, and cannot be resolved by the wavelength of the light source in the inspection apparatus. The mark 92 is used in the alignment using the contrast with the region where the second pattern 91 is arranged. The second pattern 91 is a non-functional circuit formed in a region (scribe region), which is physically cut after being imprinted to the wafer.

Programmed defects 93, 94, 95, and 96 are provided in the region where the second pattern 91 is formed. Referring to FIG. 7, the programmed defects 93 and 95 simulate the broken pattern defect caused by the disconnection of the pattern, and the programmed defects 94 and 96 simulate the pattern bridge defect caused by a short-circuit of the pattern. The programmed defects 93 and 94 have a dimension equal to a line width of the first pattern. On the other hand, the programmed defects 95 and 96 have a line width half the dimension of the first pattern. As described above, the optimum value of the focus offset depends on the kind, shape, and dimension of the defect. Therefore, when plural programmed defects having different kinds, shapes, and dimensions of the defect are provided in one alignment mark, the optimum focus offset can be found out as a whole defect to enhance the inspection accuracy.

FIGS. 19 to 30 illustrate other examples of the programmed defect formed in the alignment mark. The second pattern constituting the background of the programmed defect simulates the first pattern imprinted to the wafer, and has the dimension equal to that of the first pattern.

Figure 20:
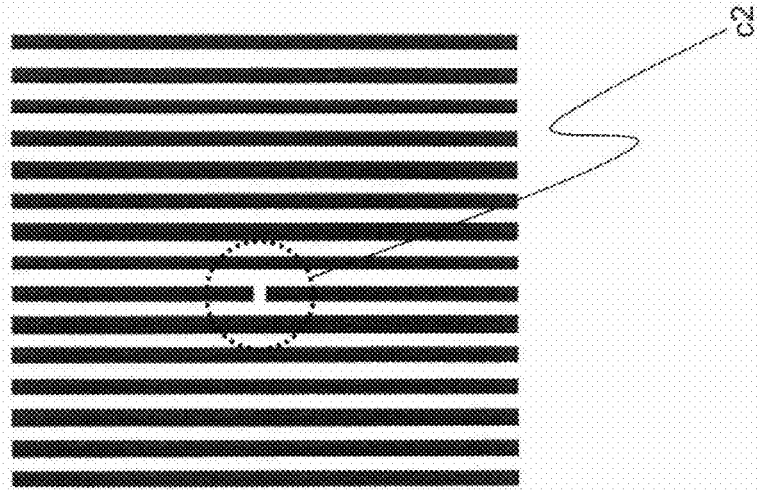
FIG. 20 is an example of the programmed defect provided in the template.
Figure 19:
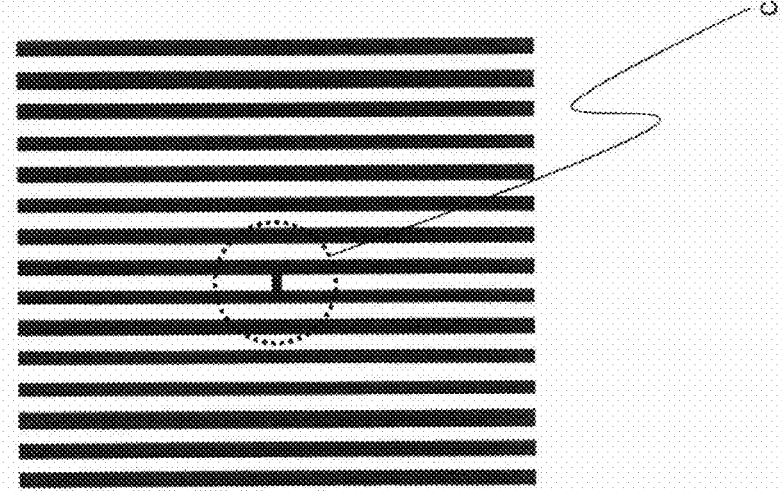
FIG. 19 is an example of the programmed defect provided in the template.

The programmed defect in a region c1 of FIG. 19 is an example of the pattern bridge defect in which the pattern is short-circuited and the dimension of the short-circuited pattern (pattern bridge defect) is about a half line width of the first pattern. The programmed defect in a region c2 of FIG. 20 is an example of the broken pattern defect in which the pattern is open-circuited and the dimension of the broken pattern is about half the line width of the first pattern.

Figures 21, 22:
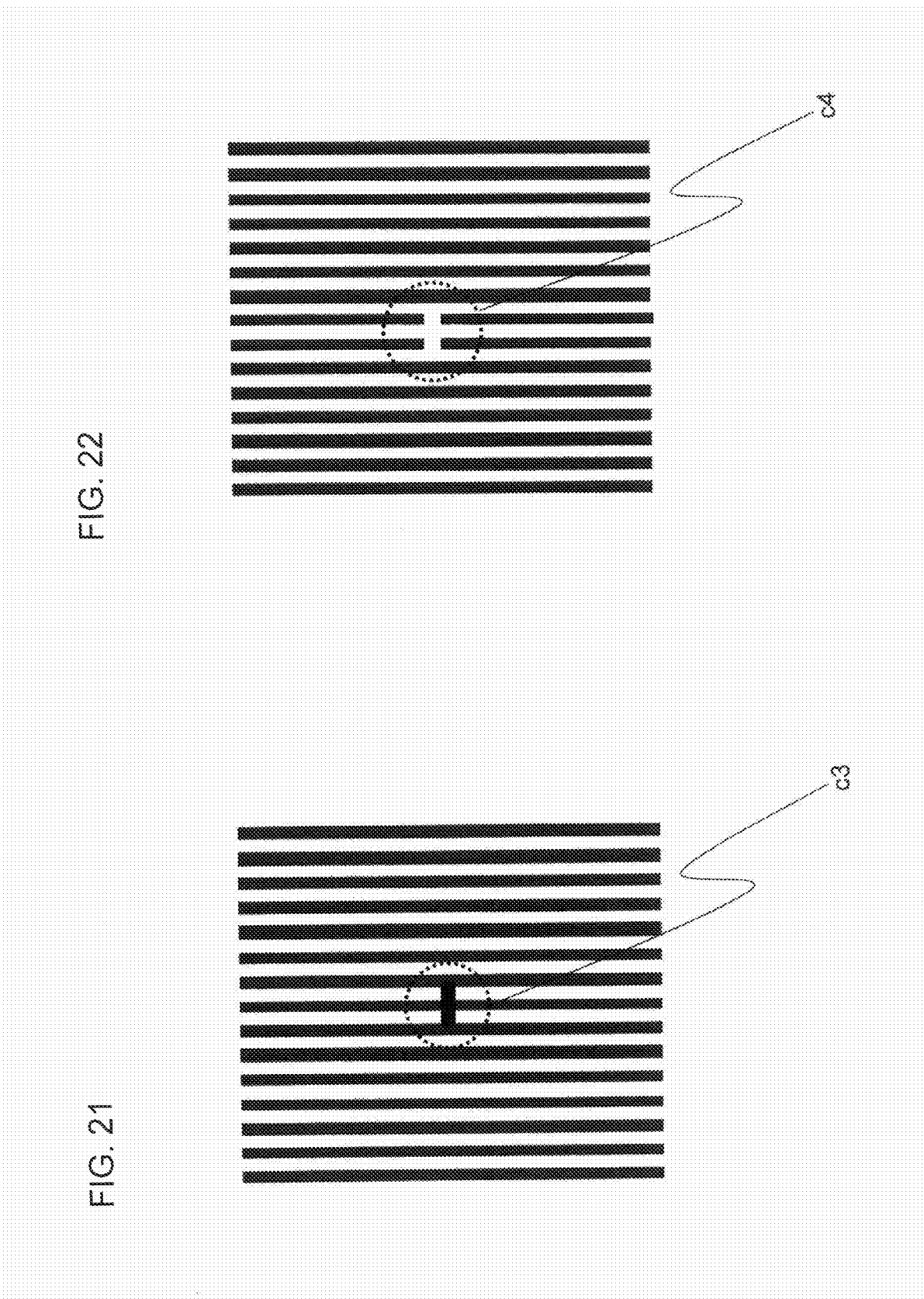
FIG. 21 is an example of the programmed defect provided in the template.
FIG. 22 is an example of the programmed defect provided in the template.
Figure 24:
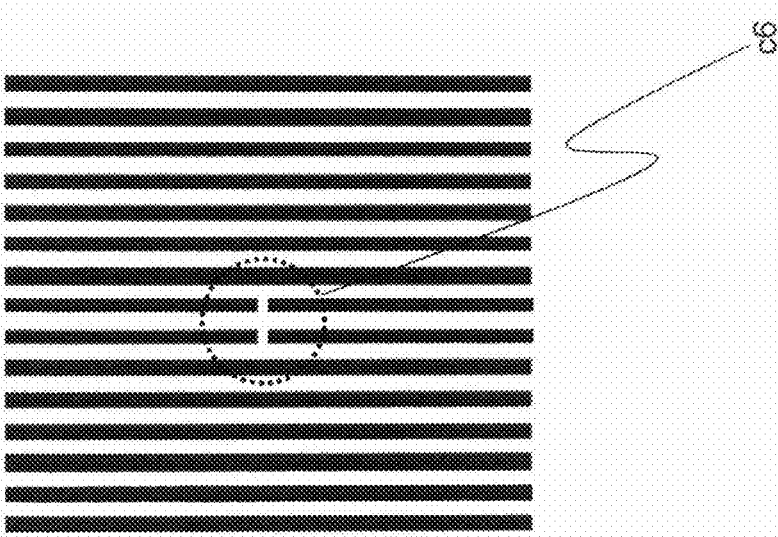
FIG. 24 is an example of the programmed defect provided in the template.
Figure 23:
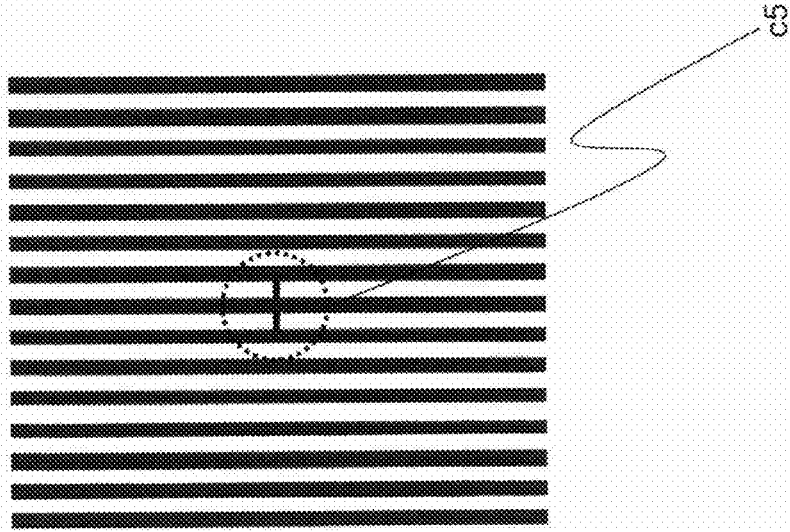
FIG. 23 is an example of the programmed defect provided in the template.

The programmed defect in a region c3 of FIG. 21 is an example of two pattern bridge defects in which the dimension of each of the short-circuited patterns generated adjacent to each other is substantially equal to the line width of the first pattern. The programmed defect in a region c4 of FIG. 22 is an example of two broken pattern defects in which the dimension of each of the broken patterns generated adjacent to each other is substantially equal to the line width of the first pattern. The programmed defect in a region c5 of FIG. 23 is an example of two pattern bridge defects in which the dimension of each of the short-circuited patterns generated adjacent to each other is about half the line width of the first pattern. The programmed defect in a region c6 of FIG. 24 is an example of two broken pattern defects in which the dimension of each of the broken patterns generated adjacent to each other is about a half line width of the first pattern.

FIGS. 21 to 24 illustrate the examples in which the two defects are generated adjacent to each other. Additionally, the programmed defect in which three or four defects are generated adjacent to one another may be provided. When the plurality of defects having the same kinds and different dimensions are provided, the programmed defect can be used as a rough indication whether defect detection sensitivity of the inspection apparatus changes. Specifically, in the case that a signal of the programmed defect changes temporally according to the dimension when an optical image of the programmed defect is captured with the inspection apparatus, preferably the inspection is stopped without performing a process of acquiring the optical image of the first pattern to inspect the existence or non-existence of the defect. For example, although the inspection apparatus can initially detect all the programmed defects, the inspection apparatus cannot detect the two programmed defects generated adjacent to each other by the short-circuited pattern because of the temporal change of the detection sensitivity, while the inspection apparatus detects the three programmed defects generated adjacent to one another by the short-circuited pattern. For example, the degradation of the defect detection sensitivity is attributed to the fact that a light amount of the light source is decreased or a vibration is generated in the table. Then, in such cases, it is desirable to stop the focal offset adjustment process, without continuing the inspection process to diagnose the inspection apparatus.

Figure 25:
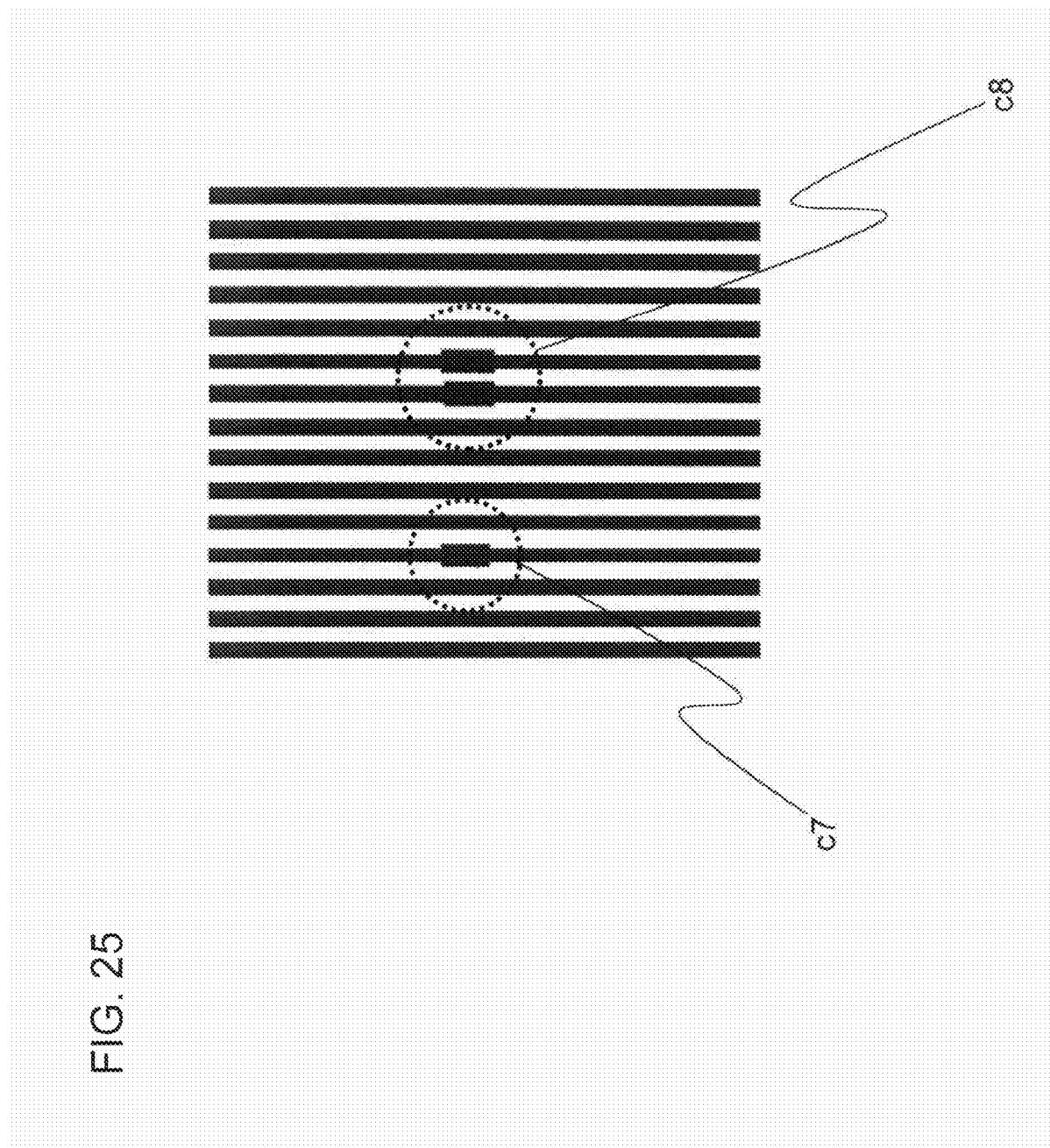
FIG. 25 is an example of the programmed defect provided in the template.
Figure 26:
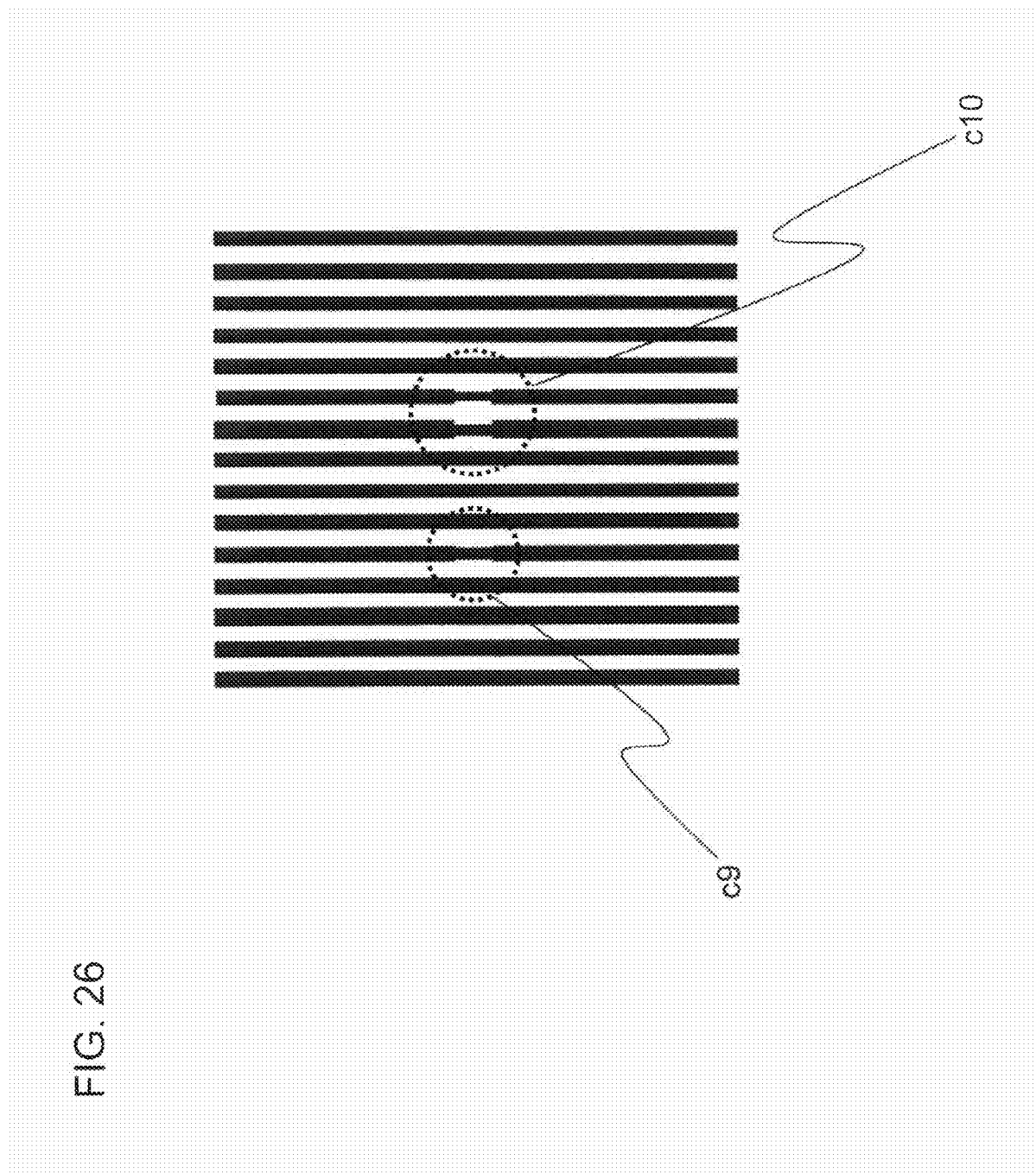
FIG. 26 is an example of the programmed defect provided in the template.

FIG. 25 illustrates an example that intentionally makes the defect in which the line width of the line pattern is locally widened. Referring to FIG. 25, the case that the defect is generated in isolation as illustrated in a region c7 and the case that the two defects are generated adjacent to each other as illustrated in a region c8 are simultaneously provided. On the other hand, FIG. 26 illustrates an example that intentionally makes the defect in which the line width of the line pattern is locally narrowed. Referring to FIG. 26, the case that the defect is generated in isolation as illustrated in a region c9 and the case that the two defects are generated adjacent to each other as illustrated in a region c10 are simultaneously provided.

In the examples of FIGS. 25 and 26, defects having various dimensions different from a design dimension may be arranged in a direction in which two edges constituting the line pattern extend. Therefore, similarly to the descriptions in FIGS. 21 to 24, the programmed defect can be used as a rough indication as to whether the defect detection sensitivity of the inspection apparatus changes.

In the case that the defects having various dimensions different from the design dimension are arranged to observe the change in defect detection sensitivity of the inspection apparatus, a reference dimension of the defect is determined, and the defect having the dimension larger than the reference dimension and the defect having the dimension smaller than the reference dimension may be provided.

Figure 27:
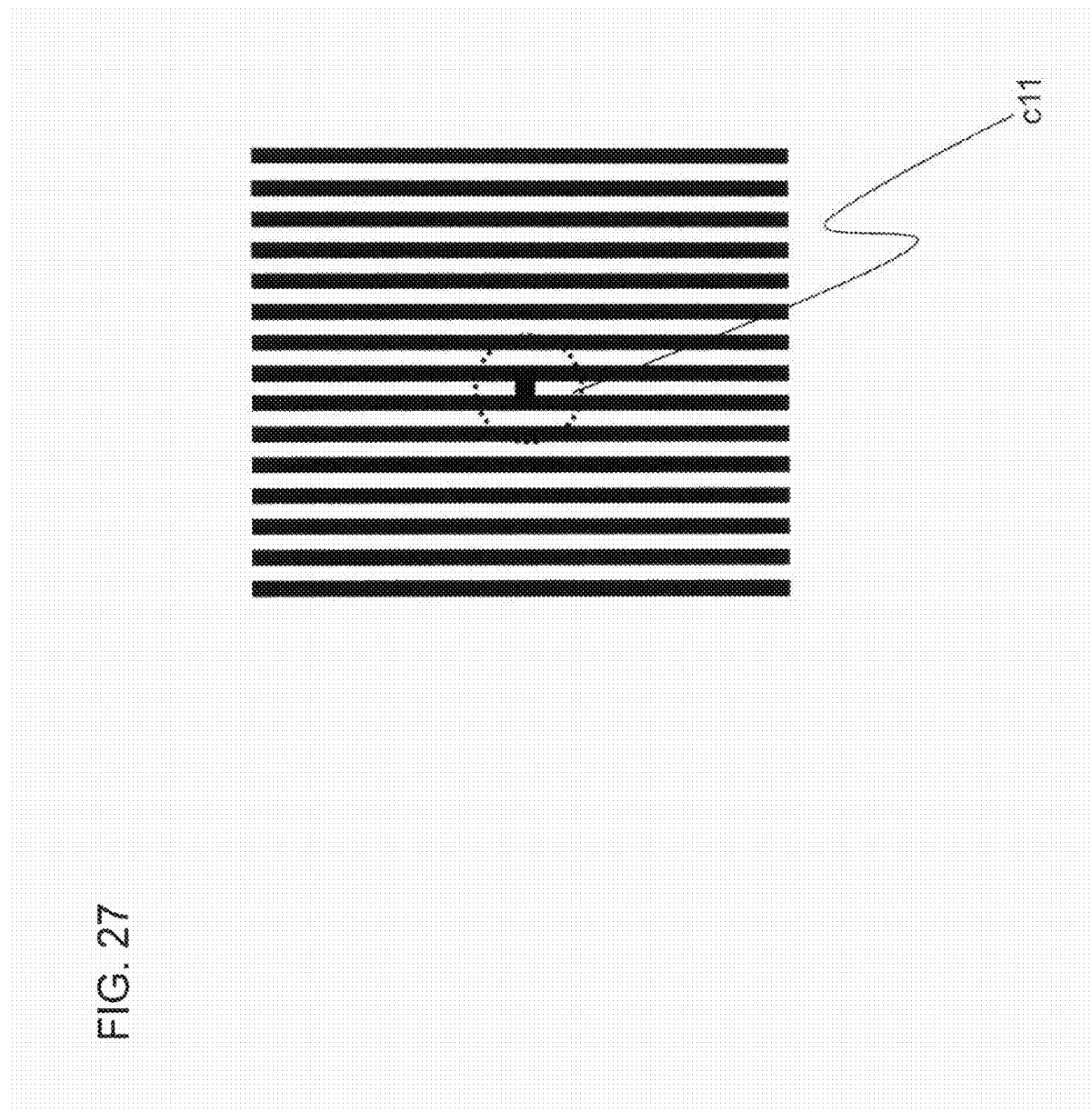
FIG. 27 is an example of the programmed defect provided in the template.
Figure 28:
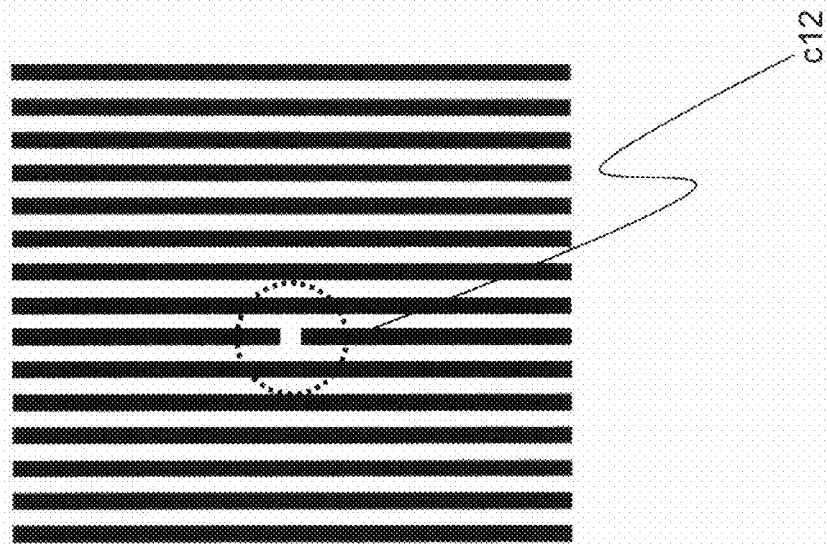
FIG. 28 is an example of the programmed defect provided in the template.
Figure 29:
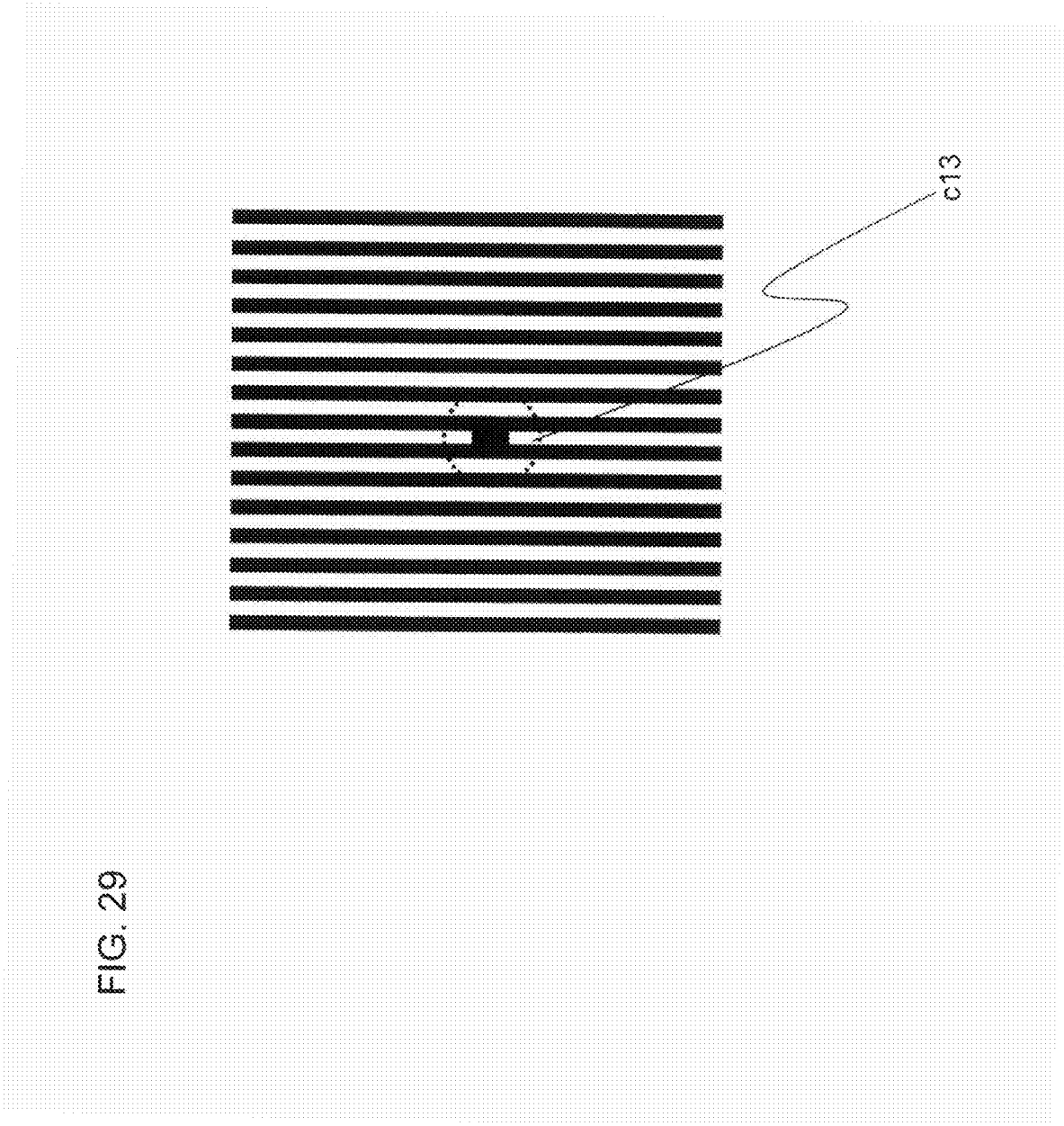
FIG. 29 is an example of the programmed defect provided in the template.
Figure 30:
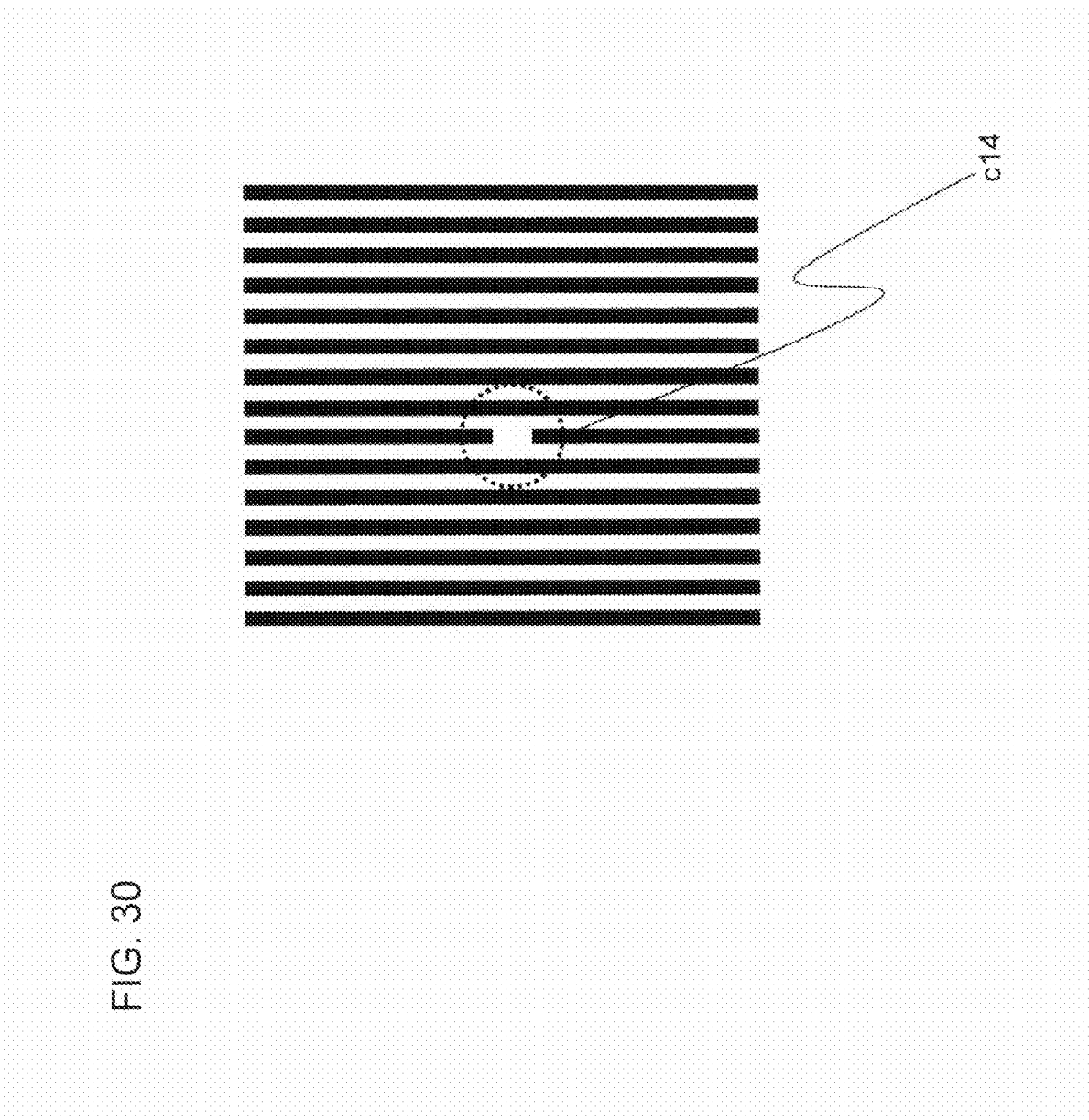
FIG. 30 is an example of the programmed defect provided in the template.

The programmed defect in a region c11 of FIG. 27 is an example of the pattern bridge defect in which the pattern is short-circuited and the dimension of the short-circuited pattern is substantially equal to the line width of the first pattern. The programmed defect in a region c12 of FIG. 28 is an example of the broken pattern defect in which the pattern is open-circuited and the dimension of the broken pattern is substantially equal to the line width of the first pattern. Based on the defect having the dimension equal to the line width of the first pattern, the defect having the dimension larger than the reference dimension and the defect having the dimension smaller than the reference dimension can be determined. The programmed defect in a region c13 of FIG. 29 is an example of the pattern bridge defect in which the pattern is short-circuited and the dimension of the short-circuited pattern is about double the line width of the first pattern. The programmed defect in a region c14 of FIG. 30 is an example of the broken pattern defect in which the pattern is open-circuited and the dimension of the broken pattern is about double the line width of the first pattern. FIGS. 29 and 30 illustrate the examples of the defect having the larger dimension. FIGS. 21 and 22 also illustrate the examples of the defect having the larger dimension. On the other hand, FIGS. 19 and 20 illustrate the examples of the defect having the smaller dimension.

Figure 8:
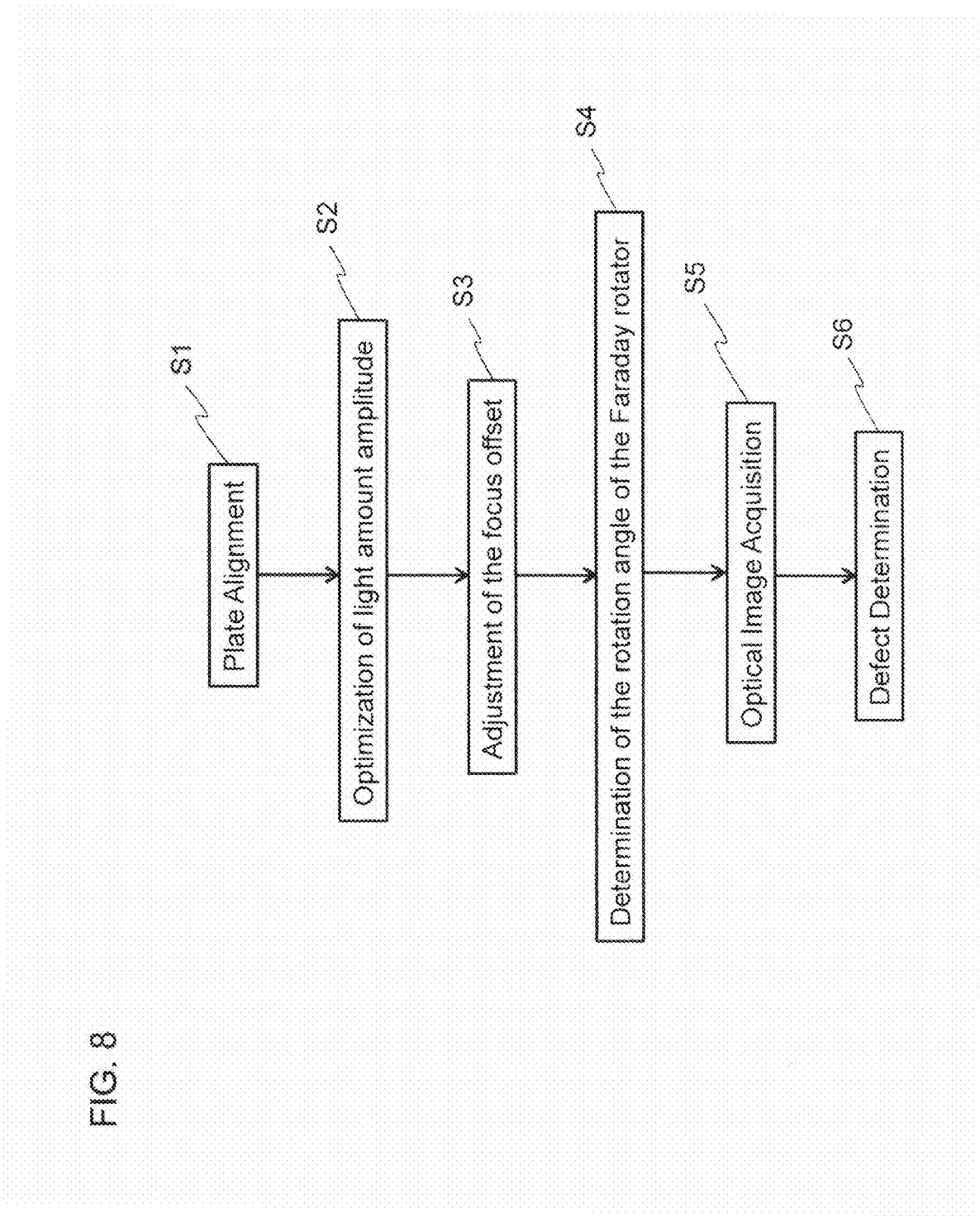
FIG. 8 is a flowchart illustrating the inspection method according to the first embodiment.

Next, the inspection method according to the present embodiment will be described. FIG. 8 is a flowchart illustrating the inspection method.

The repetitive pattern such as the line-and-space pattern, namely, the regular pattern that is periodically repeated is formed in the region to be inspected of the template. At least a part of the pattern is the pattern (first pattern) finer than the resolution limit of the optical system in the inspection apparatus. A pattern formed in a memory mat portion of a semiconductor chip can be cited as an example of the pattern. A resolution limit (R) of the optical system in the inspection apparatus is expressed by an equation (3) using a wavelength (λ) of the light from the light source and a numerical aperture (NA) of the objective lens that forms the image of the light on an inspection region of the template.

$$R = k_1 \frac{\lambda}{NA} \quad (3)$$

The alignment marks are arranged in the four corners of the imprint surface of the template. The alignment mark includes the second pattern and the region where the second pattern is not arranged but a mark used in the alignment using the contrast with the region where the second pattern is arranged, is formed. The second pattern simulates the first pattern, which is formed in the region to be inspected and is finer than the resolution limit of the optical system. The programmed defect is provided in the region where the second pattern is formed. The specific examples of the second pattern, the mark used in the alignment, and the programmed defect are described above with reference to FIG. 7.

In an inspection method of the first embodiment, the inspection target template is placed on the table of the inspection apparatus to perform the plate alignment (S1).

Light amount amplitude is optimized with respect to a sensor of the inspection apparatus that acquires the optical image of the template (S2). For example, in the case that a line sensor, in which CCD cameras of the imaging elements are arrayed in line is used as the sensor, amplifier gain of each element is adjusted such that signal amplitude of each element of the line sensor is equalized. An offset and amplitude of the brightness are adjusted such that a defect signal is detected as high as possible by maximally utilizing a dynamic range of monochrome amplitude of the optical image of the template.

The focus offset is adjusted using the programmed defect of the alignment mark provided in the imprint surface of the template (S3). Specifically, the optical image of the programmed defect is captured while a focal distance between the imprint surface of the template and the optical system (objective lens) of the inspection apparatus is changed, and the focal distance optimum for detecting the programmed defect, namely, the focal distance in which S/N becomes the maximum is obtained. The focal distance deviates from a focusing position by the focus offset.

For example, it is considered that plural chip patterns having the identical configuration are arranged in a part or whole of the template. More specifically, it is considered that the repetitive patterns of the integrated circuit imprinted to the semiconductor wafer are arranged. At this point, a repetitive unit is a rectangle having the identical dimension, and the repetitive unit is called a die when the repetitive units are separated from each other. Usually one-unit integrated circuit is formed in one die. When the repetitive pattern is inspected by the die-to-die comparison method, the optical images of the different chips having the identical pattern are compared to each other. For example, when the optical image of an nth chip is set to the inspection target, the optical image of an (n−1)-th chip is a reference image to be compared. At this point, when the repetitive pattern is the pattern that cannot be resolved by the wavelength of the light source in the inspection apparatus, the optical images having the even gray tone are compared to each other in the inspection region that does not have a defect. However, in the optical image in which the defect exists in the pattern, the defect is observed as a white bright spot or a black spot according to the kind or shape of the defect.

For example, the template is irradiated with the light, and the light reflected from the template is incident on the sensor to acquire the optical image of the repetitive pattern. At this point, when the adjacent patterns are connected to each other to generate the pattern bridge defect, the light is reflected in a wider area at the defect location, the defect is observed as the white bright spot. On the other hand, when the broken portion is generated in the pattern, because the pattern is lacking in the broken portion, the reflection area of the light is reduced, and the defect is observed as the black spot. In these examples, when the focus offset is changed, the shape of the white bright spot or black spot changes at the defect location, or the maximum or minimum amplitude of the defect signal changes.

The focus offset optimum for detecting the defect is searched in the focus offset adjusting process. Specifically, as described above, the optical image of the programmed defect provided in the alignment mark is captured while the focus offset is changed, namely, while the focal distance between the imprint surface of the template and the optical system (objective lens) of the inspection apparatus is changed, and the focus offset in which the strongest defect signal is obtained is searched with respect to the gray tone of a base. For example, a method for calculating a brightness signal level of the defect to the gray tone signal level using a predetermined algorithm is adopted.

Examples of a factor affecting the focus offset include a dimension of the pattern, which is formed in the template to be imprinted to the wafer, an engraving depth in the imprint surface, and a template surface coating condition in addition to the kind, shape, and dimension of the defect. In the inspection apparatus, depending on a state of a lighting optical system that irradiates the template with the light from the light source or an image forming optical system, which forms the image of the light transmitted or reflected by the template and causes the light to be incident on the sensor, the optimum position of the focus offset to defects such as the broken pattern defect is different from the optimum position of the focus offset to defects such as the pattern bridge defect. In such cases, it is preferred that the inspection is performed twice, for example, the inspection is performed with the optimum focus offset for the pattern bridge defect after the inspection is performed with the optimum focus offset for the broken pattern defect.

When the optimum focus offset is determined as a result of the search, the focal distance between the imprint surface of the template and the optical system (objective lens) of the inspection apparatus is adjusted such that the optimum focus offset is obtained. At this point, the focal distance is changed by adjusting a height of the table on which the template is placed in the inspection apparatus.

Figure 9:
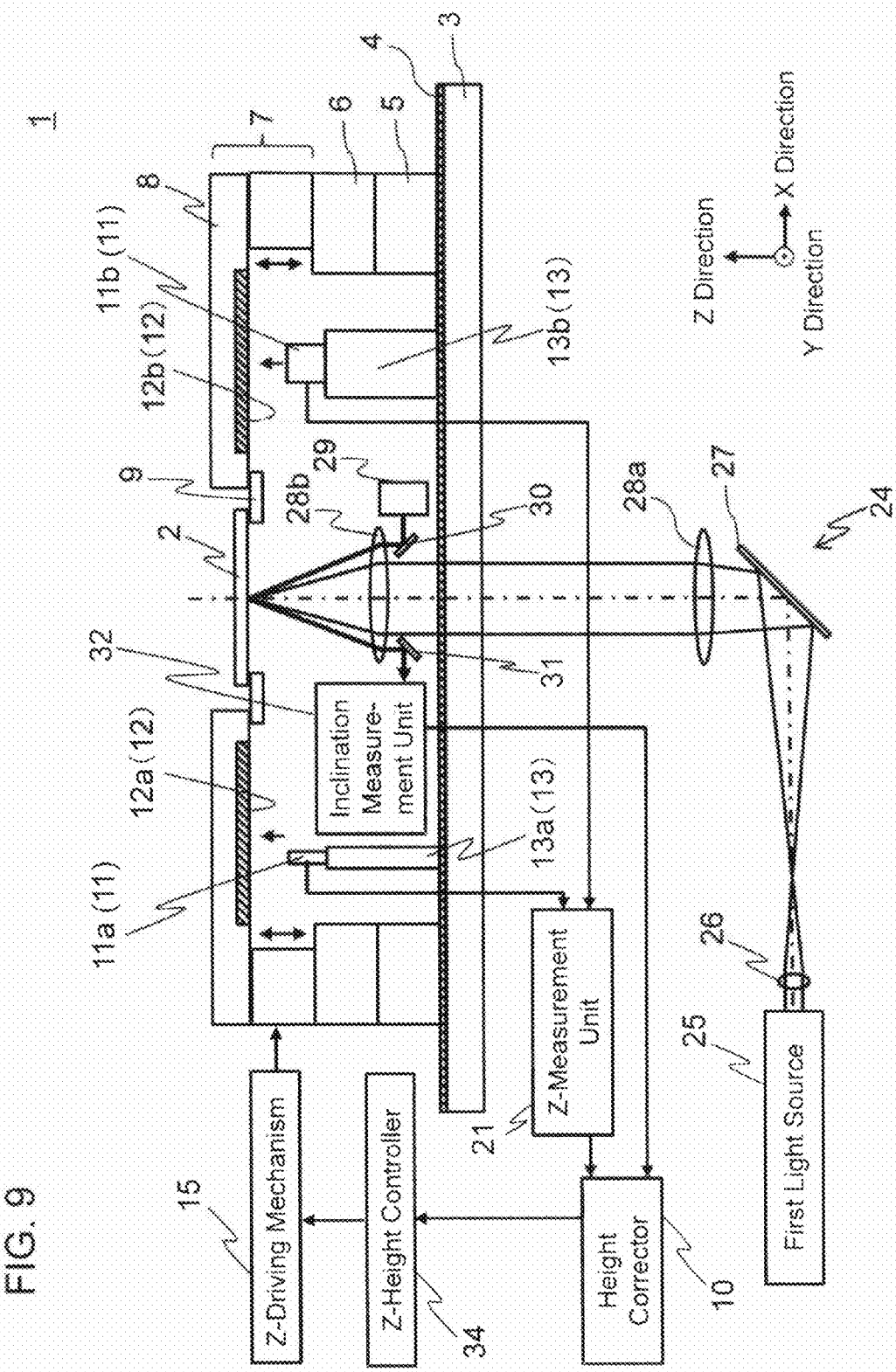
FIG. 9 illustrates an example of the table in the inspection apparatus according to the first embodiment.

FIG. 9 illustrates an example of the table in the inspection apparatus. A base 3 of a table 1 constitutes a Z-reference plane 4 in which a top surface becomes a height reference of the table 1. A Y-table 5 and an X-table 6 are arranged on the Z-reference plane 4, and a Z-table 7 is arranged on the X-table 6. The Z-table 7 is movable in the vertical direction, and the Y-table 5 and the X-table 6 are movable in the horizontal direction. Although not illustrated, the table 1 is also rotatable in a θ-direction.

The Z-table 7 includes a support 8 in an upper portion thereof. A support body 9 that supports a template 2 is provided in the support 8. The template 2 is arranged such that a mesa formed in the pattern is oriented toward the side of the Z-reference plane 4 of the base 3.

The Z-table 7 includes three Z-driving mechanisms 15 so as to correspond to the position of the support body 9 in the support 8. In the Z-table 7, the support 8 is vertically moved along a height direction by the Z-driving mechanism 15.

In the support 8 of the Z-table 7, two measuring surfaces 12 including a first measuring surface 12a and a second measuring surface 12b are provided in a surface facing the Z-reference plane 4. The first measuring surface 12a and the second measuring surface 12b are provided so as to become coaxial and are aligned across a measuring position that is of the inspection position of the template 2.

A Z-sensor 11 includes a first Z-sensor 11a and a second Z-sensor 11b that are provided on the Z-reference plane 4 so as to correspond to the positions of the first measuring surface 12a and second measuring surface 12b. The first Z-sensor 11a and the second Z-sensor 11b are provided on the Z-reference plane 4 while placed on base portions 13a and 13b (constituting a base 13).

The heights of the first Z-sensor 11a, second Z-sensor 11b, and base portions 13a and 13b are already known. Accordingly, using these values, the height of the first measuring surface 12a from the Z-reference plane 4 is measured with the first Z-sensor 11a, and the height of the second measuring surface 12b from the Z-reference plane 4 is measured with the second Z-sensor 11b.

For signals output from the first Z-sensor 11a and the second Z-sensor 11b, a Z-measurement unit 21 connected to the first Z-sensor 11a and the second Z-sensor 11b converts a current value into a voltage value. After the voltage value is amplified to a proper voltage level by a non-inverting amplifier, an A/D converter converts the amplified voltage into digital data, thereby producing height data of the first measuring surface 12a and second measuring surface 12b.

An inclination measurement unit 32 produces a Z-map expressing inclination, torsion, and waviness states of the imprint surface of the template 2 based on the height data.

The height data of the first measuring surface 12a and the height data of the second measuring surface 12b, which are produced by the Z-measurement unit 21, are sent to a height corrector 10 connected to the Z-measurement unit 21 and used to control the movement of the Z-table 7. The information on the focus offset searched in S3 of FIG. 8 is also sent to the height corrector 10. A Z-height controller 34 controls the Z-driving mechanism 15 based on the information from the height corrector 10, and adjusts the height of the Z-table 7 such that the template 2 is located at the position of the optimum focus offset.

In the case that the focus offset adjusted in S3 of FIG. 8 changes depending on an X-coordinate and a Y-coordinate because the imprint surface of the template is not horizontal, the Z-table 7 is controlled based on the Z-map produced by the inclination measurement unit 32, and a Z-coordinate is changed according to the changes of the X-coordinate and Y-coordinate such that the focus offset is always maintained at a proper value.

Figure 10:
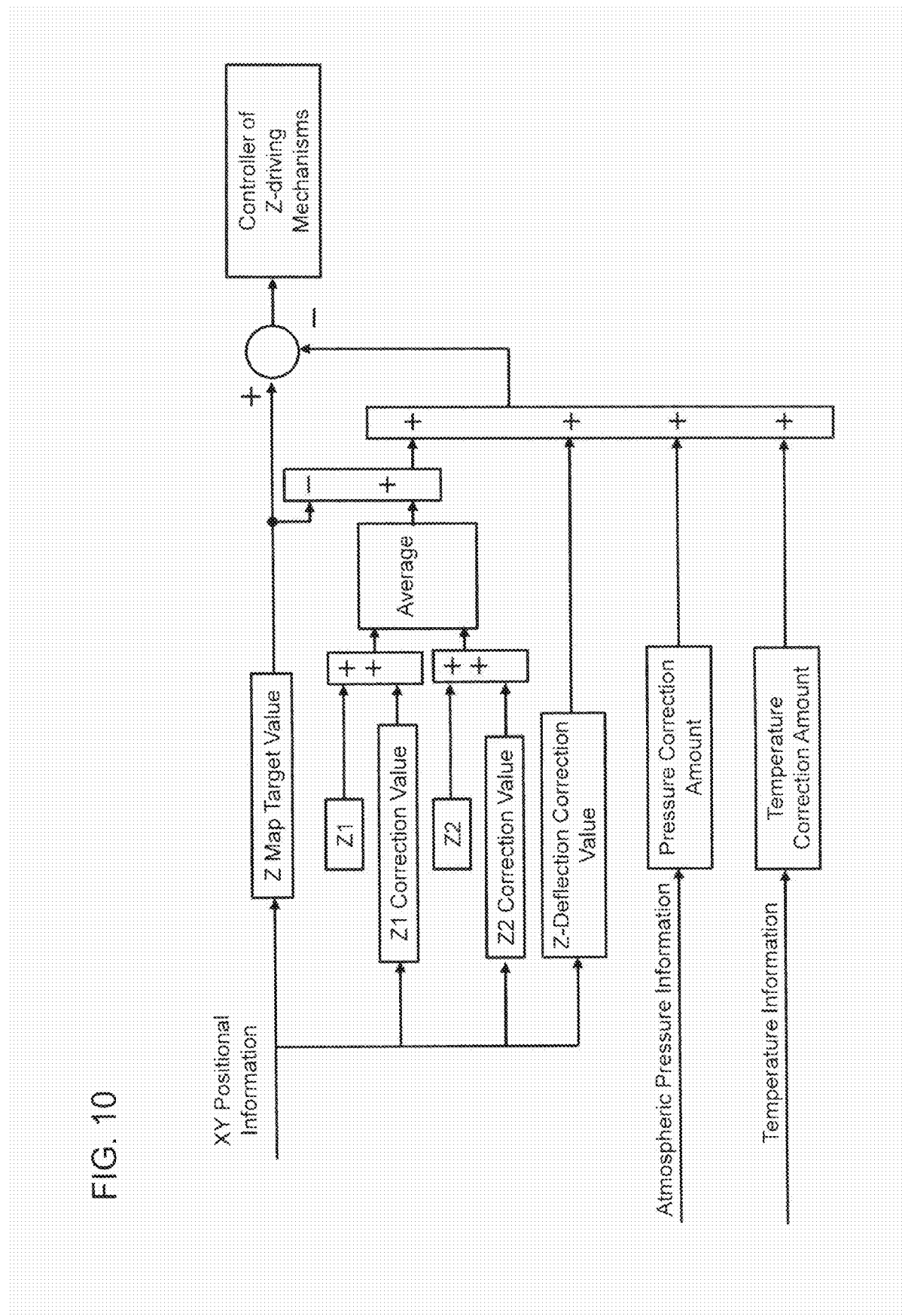
FIG. 10 is a block diagram illustrating a control method for correcting the height of the template using the corrected Z-map.

FIG. 10 is a block diagram illustrating a control method for correcting the height (Z) of the template 2 using the corrected Z-map. In other words, FIG. 10 illustrates a function of the height corrector 10 of the table 1 in FIG. 9, and illustrates a method in which the table 1 adjusts the template 2 to the target height position.

As illustrated in FIG. 9, the template 2 is placed on the Z-table 7. The Z-table 7 is movable in the horizontal direction by the Y-table 5 and the X-table 6. The moving positions of the Y-table 5 and X-table 6 are measured with a laser interferometer (not illustrated), and sent to the height corrector 10 as XY-information data.

Using the Z-map, the height corrector 10 of the table 1 obtains the data of the target height (Z-map target value) at the measuring position (inspection position) of the template 2 from the XY-position information on the Y-table 5 and X-table 6. Based on the height data, the height corrector 10 controls the Z-driving mechanism 15 of the Z-table 7 using the Z-height controller 34, and adjusts the height of the template 2 to the target height (Z-map target value).

In the case that the height (Z) position of the template 2 is adjusted to the target position with higher accuracy, as illustrated in FIG. 10, a Z-map target value is corrected, and the Z-height of the template 2 is adjusted based on the corrected Z-map target value.

For example, a height (Z1) at the position corresponding to the measuring position in the first measuring surface 12a of the Z-table 7 and a correction value (Z1 correction value) in which an influence of a gravitational deflection on the first measuring surface 12a is considered are added by an arithmetic circuit (not illustrated) of the height corrector 10. Similarly, a height (Z2) at the position corresponding to the measuring position in the second measuring surface 12b of the Z-table 7 and a correction value (Z2 correction value) in which the influence of the gravitational deflection on the second measuring surface 12b is considered are added. The arithmetic circuit of the height corrector 10 calculates an average value of the correction value regarding the first measuring surface 12a and the correction value regarding the second measuring surface 12b, and sets the average value to a correction amount in the correction in which the measuring surface 12 is used.

In another correction, a Z-deflection correction value is calculated in consideration of the gravitational deflection of the template 2. In still another correction, an atmospheric pressure correction amount or a temperature correction amount is calculated.

The amount of the correction in which the measuring surface 12 is used, the Z-deflection correction value, the atmospheric pressure correction amount, and the temperature correction amount are added to calculate the correction data by the arithmetic circuit of the height corrector 10.

In the height corrector 10, the arithmetic circuit calculates a difference between the data of the Z-map target value at the measuring position of the template 2 and the correction data to obtain the corrected Z-map target value. As a result, as illustrated in FIG. 10, based on the corrected Z-map target value, the height corrector 10 controls the Z-driving mechanism 15 of the Z-table 7 using the Z-height controller 34, and adjusts the height of the template 2 to the target height.

Referring to FIG. 9, an optical system 24 is arranged below the template 2. The optical system 24 is arranged in order to optically inspect the template 2 in the case that the inspection apparatus is constructed using the table 1.

In the optical system 24, the light emitted from a first light source 25 is transmitted through a lens 26, the orientation of the light is changed by a mirror 27, and the light is collected in the inspection position of the template 2 by lenses 28a and 28b. The light reflected onto the lower side of the template 2 is collected to form the image by a TDI (Time Delay and Integration) sensor, thereby generating the optical image used in the inspection of the inspection apparatus.

In the optical system 24, a second light source 29 emits height measuring light toward the template 2. The orientation of the light emitted from the second light source 29 is changed by a mirror 30, and the inspection position on the template 2 is irradiated with the light. Then, the light is incident on the inclination measurement unit 32 by a mirror 31 after being reflected by the template 2.

Thus, some of constituents of the optical system 24 in FIG. 9 are also used to measure the height of the template 2. The use of the optical system 24 common to the inspection and the height measurement can accurately adjust the template 2 to the target height in the table 1. In the inspection apparatus provided with the table 1, the inspection is performed while the template 2 and the optical system 24 are maintained at the proper focus offset positions, so that the template 2 can accurately be inspected.

In the inspection method of the present embodiment, processes in S4 to S6 of FIG. 8 are performed after the focal distance between the template 2 and the objective lens is controlled by adjusting the focus offset in S3 of FIG. 8. More particularly, in an inspection apparatus 100 of FIG. 14, a rotation angle of a light polarization plane by a Faraday rotator 204 is determined (S4), the optical image is acquired for the purpose of the inspection (S5), and the defect determination is made based on the optical image acquired in S5 (S6).

Particularly, in the process of S4, the gradation value is obtained in each pixel with respect to the optical image of the pattern of the template 2, which is captured on a predetermined condition, and the rotation angle of the light polarization plane by the Faraday rotator is determined such that a standard deviation of the gradation values is minimized. In the process of S4, on an as needed basis, the rotation angle may be acquired when a value, in which the standard deviation of the gradation values in a plurality of optical images that are acquired by changing the rotation angle of the light polarization plane by the Faraday rotator is divided by a square root of an average gradation value obtained from the gradation values, becomes the minimum. Preferably the optical image of the programmed defect provided in the alignment mark of the first embodiment is used in both cases.

The processes in S4 to S6 will be described in detail below. The processes in S1 to S3 previously described and the above-mentioned S4 correspond to those performed in advance of the inspection, namely, a process preceding the inspection.

Figure 14:
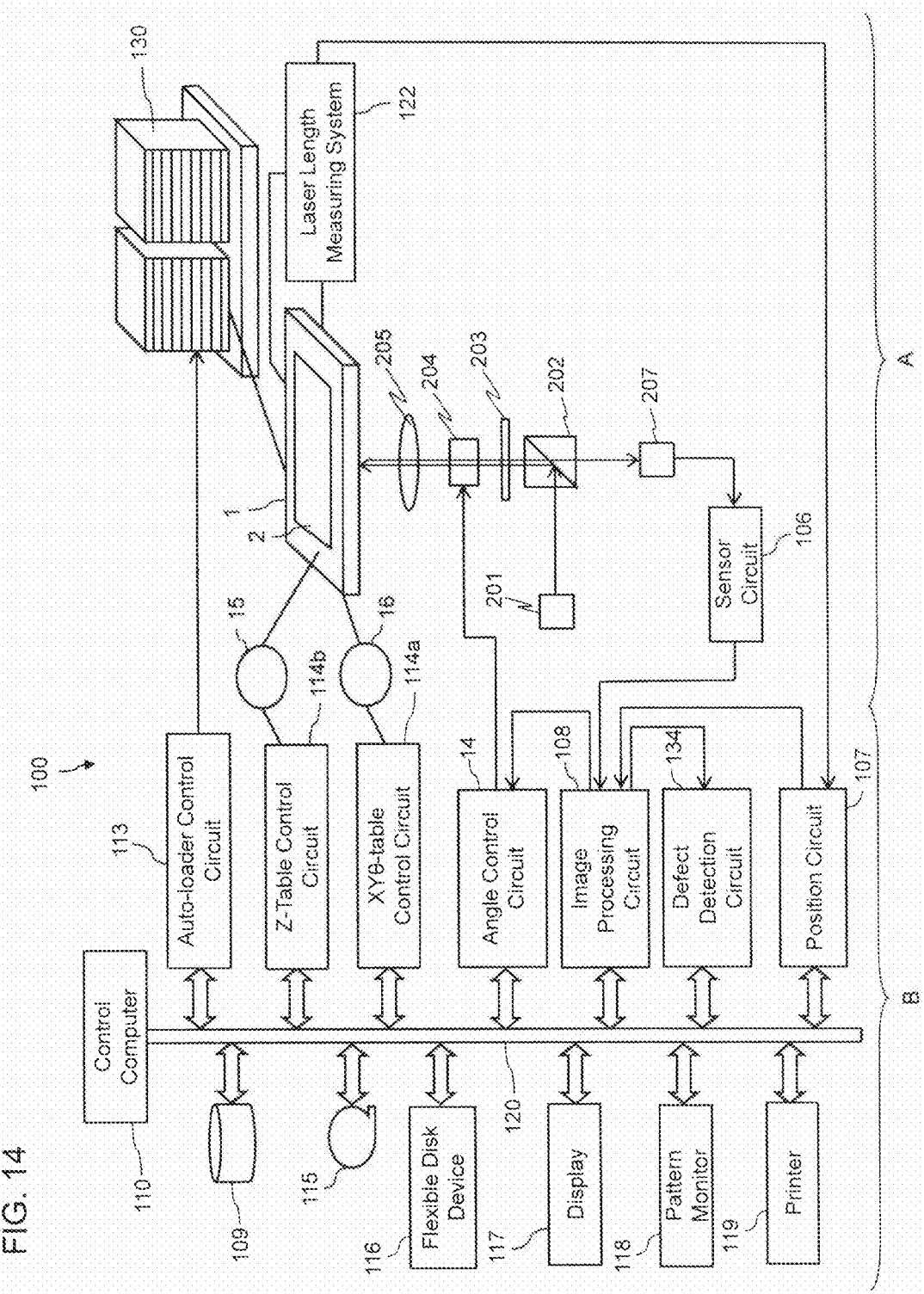
FIG. 14 is a schematic configuration diagram of the inspection apparatus according to the first embodiment.

FIG. 14 is a schematic configuration diagram of an inspection apparatus 100 according to the present embodiment. As illustrated in FIG. 14, an inspection apparatus 100 includes a configuration unit A that constitutes an optical image acquisition circuit and a configuration unit B that performs processing necessary for an inspection using an optical image acquired by the configuration unit A.

In the configuration unit A, the table 1 described with reference to FIG. 9 is used as the table on which the template 2 is placed. Therefore, the table 1 (not illustrated in FIG. 14) includes the XYθ-table that is movable in the horizontal direction and the θ-direction and the Z-table that is movable in the vertical direction. The configuration of the optical system 24 in FIG. 9 differs from the optical system in FIG. 14.

In the configuration unit B, the control computer 110, that is, the controller controlling the whole of the inspection apparatus 100 is connected to a position circuit 107, a image processing circuit 108, an angle control circuit 14, defect detection circuit 134, an auto-loader control circuit 113, an XYθ-table control circuit 114a, a Z-table control circuit 114b, a magnetic disk drive 109 as one example of storage, a magnetic tape device 115, a flexible disk device 116, a display 117, a pattern monitor 118, and a printer 119 through a bus 120 that constitutes a data transmission line.

In the configuration unit A, the XYθ-table is driven by an XYθ-driving mechanism 16 that is controlled by an XYθ-table control circuit 114a. The Z-table is driven by the Z-driving mechanism 15 that is controlled by a Z-table control circuit 114b. A moving position of the stage 1 is measured by the laser length measuring system 122, and transmitted to the position circuit 107. The template 2 located on the table 1 is automatically conveyed by the auto-loader 130 that is driven by the auto-loader control circuit 113, and then the template 2 is automatically discharged after the inspection is finished.

The auto-loader 130 automatically conveys the template 2, and automatically discharges the template 2.

The optical image of the pattern of the template 2, that is the inspection object, is acquired in the configuration unit A. Specifically, it will be described as follows.

Referring to FIG. 14, the light emitted from a light source 201 of the configuration unit A is reflected by a polarization beam splitter 202, and incident on the Faraday rotator 204 through a half-wavelength plate 203. The image of the light transmitted through the Faraday rotator 204 is formed in the inspection region of the template 2 by an objective lens 205. Then, the light reflected by the template 2 is transmitted through the objective lens 205, transmitted through the Faraday rotator 204, the half-wavelength plate 203, and the polarization beam splitter 202, and incident on a sensor 207. The sensor 207 captures the optical image of the pattern of the template 2.

As for the sensor 207, a line sensor, in which imaging devices such as a photodiode are arranged in a line, can be used. In this case, the sensor 207 images a pattern of the template 2 so that the direction of the continuous movement of the table 1 coincides with the direction at which charges are stored in the TDI sensor.

The Faraday rotator 204 rotates the light polarization plane by a Faraday effect. The Faraday effect is a phenomenon in which, when a magnetic field is applied to the same direction as the light traveling direction while linearly polarized light is incident on an optical material, phase speeds of two components (right-handed circularly polarized light and left-handed circularly polarized light) of the linearly polarized light deviate from each other, and therefore the polarization plane of the light (linearly polarized light) output from the optical material rotates by the phase difference at an exit location.

As described above, among the pattern defects, the pattern bridge defect (region a1 in FIG. 11) in which the lines are short-circuited with each other and the broken pattern defect (region a2 in FIG. 12) in which the line is disconnected have a serious influence on the performance of the template. On the other hand, edge roughness observed in the region a3 of FIG. 13 has a limited influence on the template compared with the pattern bridge defect or the broken pattern defect. Therefore, the edge roughness is not necessarily detected in the inspection.

However, in the case that the pattern bridge defect, the broken pattern defect, and the edge roughness having the size that is less than the optical resolution limit are mixed in the same pattern, more particularly the same repetitive pattern having a period that is less than the optical resolution limit of the optical system in the inspection apparatus, in observation with the optical system, the brightness and darkness caused by the pattern bridge defect or the broken pattern defect is not distinguished from the brightness and darkness caused by the edge roughness. This is because, in the optical image of the pattern, all of the defects, that is, the pattern bridge defect, the broken pattern defect, and the edge roughness become blurred by the same amount, that is, these defects are expanded to the same dimension, namely, to about the optical resolution limit of size.

Figure 15:
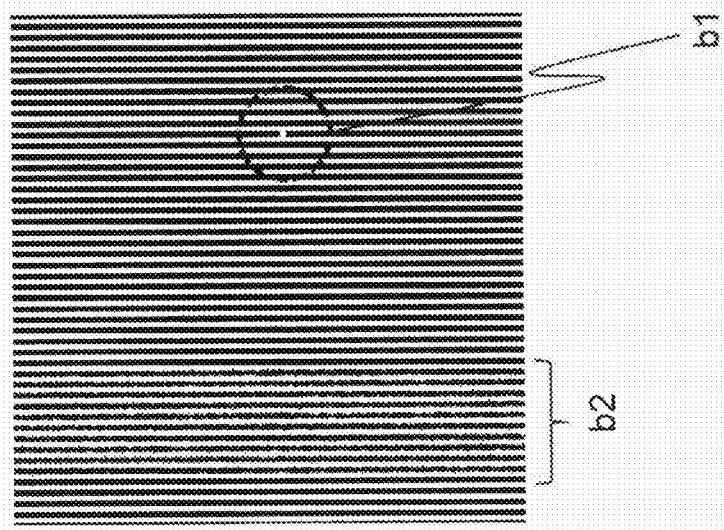
FIG. 15 schematically illustrates the line and space pattern having defects.

FIG. 15 schematically illustrates the line and space pattern provided in the template. In FIG. 15, it is assumed that the dimension of the pattern is smaller than the resolution limit of the optical system. In the region b1, the line pattern is partially lacking thus generating the broken pattern defect. In the region b2, the edge roughness of the line pattern becomes prominent. Although a difference of the defect between the broken pattern defect in the region b1 and the edge roughness in the region b2 is clearly recognized on the actual template, the differences are not distinguished from each other by the observation through the optical system. This is because the optical system behaves as a spatial frequency filter defined by a wavelength λ, of the light emitted from the light source and a numerical aperture NA.

Figure 16:
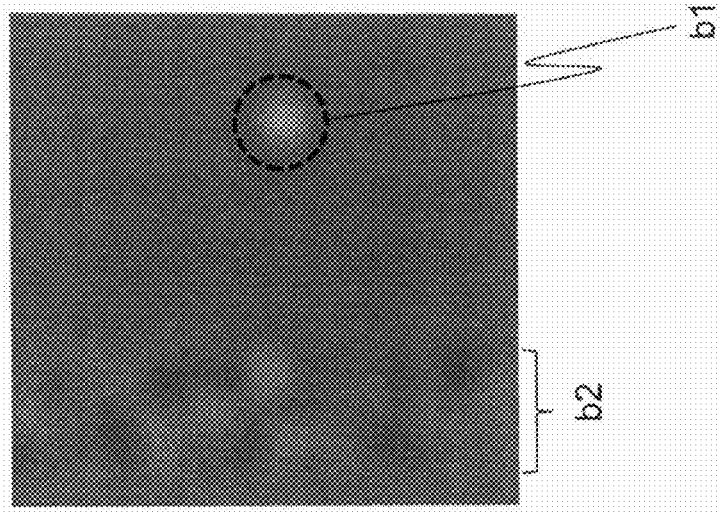
FIG. 16 illustrates a state in which the pattern in FIG. 15 is subjected to the spatial frequency filter.

FIG. 16 illustrates a state in which the pattern in FIG. 15 is subjected to the spatial frequency filter. As can be seen from FIG. 16, the defect in the region b1 and the defect in the region b2 are expanded to the similar dimension, and the shapes of the defects are not distinguishable from each other. Thus, in principle, the broken pattern defect that is less than the optical resolution limit and the edge roughness that is less than the optical resolution limit are not distinguished from each other by the optical system. The same holds true for the pattern bridge defect and the edge roughness.

The large defect such as the pattern bridge defect and the broken pattern defect has the large influence on the polarization state of the illumination light compared with the small defect such as the defect caused by the edge roughness. For example, in the pattern bridge defect in FIG. 11, a vertical direction and a horizontal direction differ from each other in sensitivity for an electric field component of the illumination light when the adjacent lines are connected to each other. Specifically, it is as follows.

For the sake of easy understanding, it is considered that the linearly-polarized light is perpendicularly incident to the template. In the case that the linearly-polarized light has the polarization direction of 45 degrees with respect to a direction along an edge of the line and space pattern, while a vertical component and a horizontal component of the electric field of the incident light are equal to each other, a difference between the horizontal component and the vertical component of the electric field of the reflected light emerges due to the pattern bridge defect, that is, the horizontal component becomes larger than the vertical component. As a result, the polarization direction of the light reflected from the pattern bridge defect becomes inclined in the direction intersecting the direction of the edge of a line-and-space pattern. Also, in the same example, in the case of the broken pattern defect, as shown in FIG. 12, the polarization direction becomes inclined in the direction along the edge of a line-and-space pattern.

Figure 13:
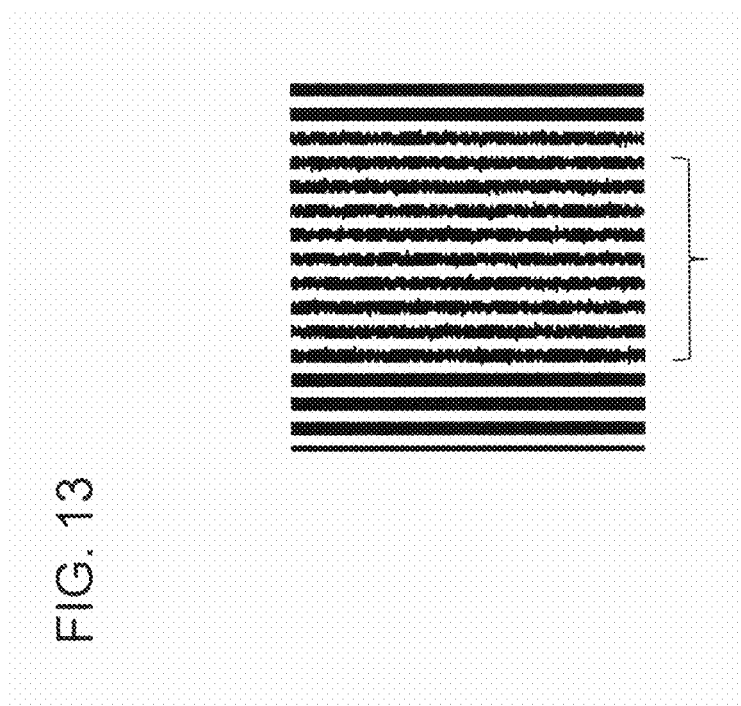
FIG. 13 illustrates an example of a defect caused by edge roughness.

On the other hand, for the defect caused by the edge roughness in FIG. 13, the adjacent lines are not connected to each other, and the lines are not disconnected. Because a size of irregularities in the edge roughness is finer than the pattern bridge defect and the broken pattern defect, sensitivity between the vertical and horizontal directions of the electric field component of the illumination light is not so large. Therefore, in the case that the linearly-polarized light is perpendicularly incident to the template, the polarization direction of the light scattered by the edge roughness becomes a value close to 45 degrees of the polarization direction of the incident light when the linearly-polarized light has the polarization direction of 45 degrees with respect to the direction along the edge of the line and space pattern. However, because the polarization direction is influenced by a base pattern having the periodic repetition, the polarization direction does not completely become 45 degrees, but the polarization direction has the value slightly deviated from 45 degrees.

The pattern bridge defect or the broken pattern defect differs from the edge roughness in the influence on the polarization state of the illumination light. Accordingly, even if the pattern is finer than the optical resolution limit of the optical system, the defect can be classified by taking advantage of the difference. Specifically, by controlling the polarization state of the illumination light and the condition for the polarization control element, that is, Faraday rotator 204 of the present embodiment, in the optical system that images the light reflected from the template, the bright and dark unevenness caused by the edge roughness can be removed with the polarization control element to extract only the change in amplitude of the pattern bridge defect or broken pattern defect.

S4 in FIG. 8 is a step for determining the rotation angle (Faraday rotation angle θ) of the polarization plane of light by the Faraday rotator 204 so as to minimize the amount of the light scattered by the edge roughness and incident on the sensor 207. The edge roughness is preferably provided in addition to a pattern bridge defect and broken pattern defect as a programmed defect of the alignment mark provided on the imprint surface of the template 2 in the present embodiment. Thus, by using the alignment mark, it is possible to determine a condition for removing non-uniformity of brightness of the light scattered by the edge roughness, that is, the Faraday rotation angle θ for minimizing the amount of the light scattered by the edge roughness and incident on the sensor 207. In addition, a programmed defect maybe at least one of a pattern bridge defect in which lines are short-circuited and a broken pattern defect in which the line is disconnected.

In the inspection apparatus 100 as shown in FIG. 14, the rotation angle (Faraday rotation angle θ) of the polarized plate of the light is changed by the Faraday rotator 204 such that the light scattered by the edge roughness of the template 2 is prevented from being incident to the sensor 207. The light scattered by the pattern bridge defect or broken pattern defect is separated from the light scattered by the edge roughness, and is incident to the sensor 207 through the half-wavelength plate 203 and the polarization beam splitter 202. Therefore, in the optical image captured with the sensor 207, the pattern bridge defect and the broken pattern defect are easily inspected, because the pattern bridge defect and the broken pattern defect are left while the bright and dark unevenness caused by the edge roughness is removed. That is, the optical image captured with the sensor 207 can be used to inspect the pattern finer than the optical resolution limit of the optical system.

Figure 17:
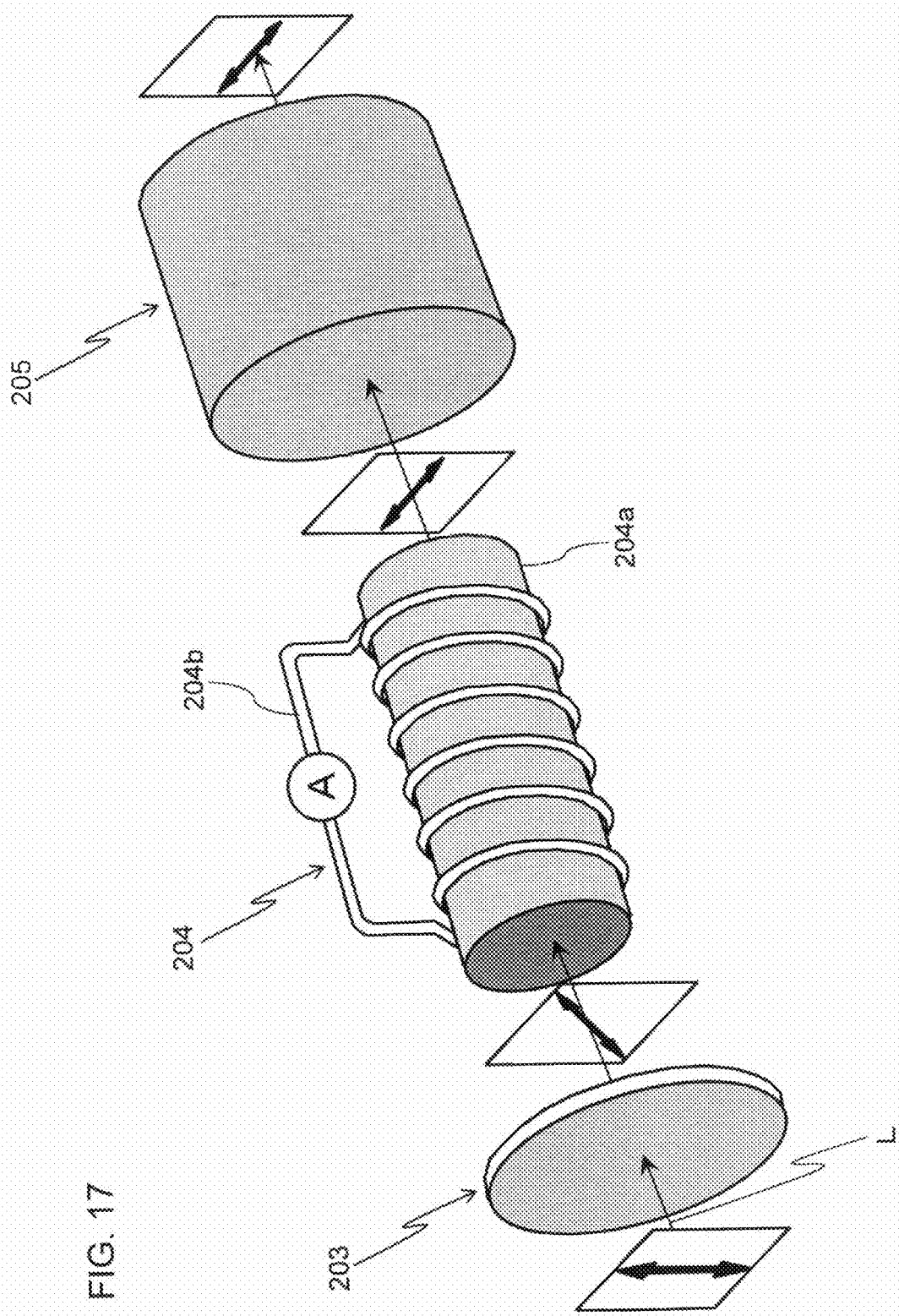
FIG. 17 illustrates a state in which a polarization plane is rotated by the optical system in the inspection apparatus.
Figure 18:
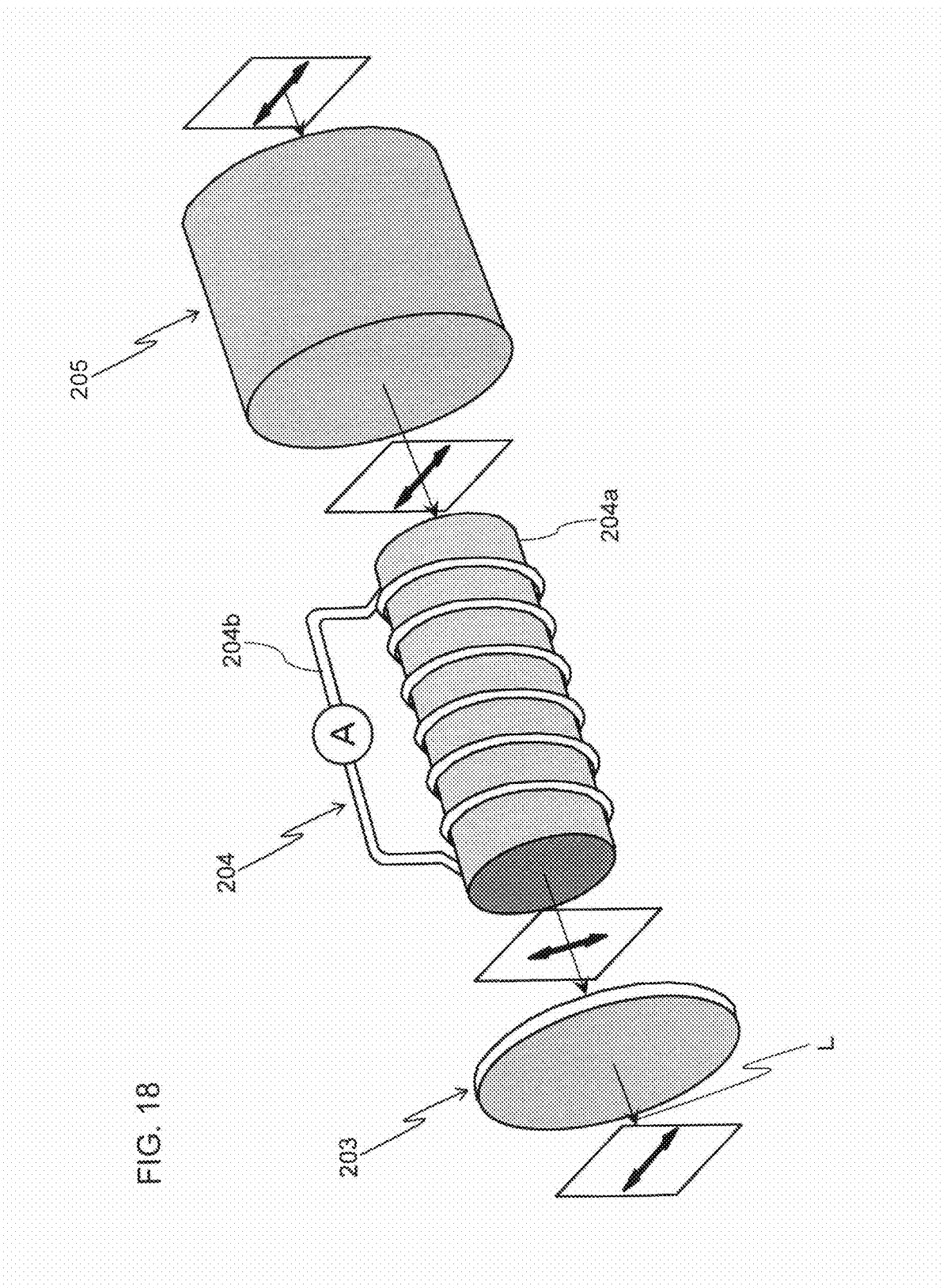
FIG. 18 illustrates a state in which a polarization plane is rotated by the optical system in the inspection apparatus.

FIGS. 17 and 18 are views illustrating the rotation of the polarization plane of light by the optical system of the inspection apparatus 100.

As shown in FIGS. 17 and 18, the Faraday rotator 204 includes an optical material 204a that transmits light, and a coil 204b is wound around the optical material 204a. The optical material 204a is a material having a high transmittance to the light emitted from the light source 201. For example, in the case that the light source 201 emits the DUV light, a magneto-optical crystal, such as $SiO_2$, $CaF_2$ or $MgF_2$ is used as the optical material 204a. The coil 204b is wound such that passage of a current applies a magnetic field to the optical material 204a in a direction parallel to a traveling direction of the light.

The rotation angle (Faraday rotation angle θ) of the polarized plate of the light rotated by the Faraday rotator 204 is changed as follows.

As illustrated in FIGS. 17 and 18, the Faraday rotator 204 includes the optical material 204a and the coil 204b wound around the optical material 204a. The intensity of the magnetic field applied to the optical material 204a is controlled by changing the current passed through the coil 204b, which allows the Faraday rotation angle θ to be changed. At this point, the Faraday rotation angle θ is expressed by the following equation (4). Where H is the intensity of the magnetic field, l is a length of a substance transmitting the polarized light, and V is called a Verdet constant that depends on a kind of the substance, the wavelength of the polarized light, and temperature.

$$\theta = VHl \quad (4)$$

For example, in the case that a material, such as $SiO_2$, $CaF_2$, and $MgF_2$, which has the high transmittance to the DUV light is used as the optical material 204a, because the material does not have spontaneous magnetization, it is necessary to apply the large magnetic field to the optical material 204a in order to obtain the desired Faraday rotation angle θ.

The Faraday rotation angle θ that properly separates the light scattered by the pattern bridge defect or the broken pattern defect from the light scattered by the edge roughness depends on the pattern structure. For this reason, in the inspection apparatus 100, the Faraday rotation angle θ is changed according to the pattern of the template 2. Specifically, an angle control circuit 14 changes the current passed through the coil of the Faraday rotator 204, and thereby the intensity of the magnetic field applied to the optical material is changed such that the Faraday rotation angle θ is obtained according to the type of the pattern.

In the case that the permanent magnet is used in the Faraday rotator, multiple permanent magnets having different intensities of the magnetic field are prepared. The permanent magnet is selected such that the Faraday rotation angle θ is obtained according to the type of the pattern, and the magnetic field necessary for the optical material is applied.

The Faraday rotation angle θ is also changed by changing a thickness of the optical material. Accordingly, multiple optical materials having different thicknesses are prepared, and the optical material that can achieve the Faraday rotation angle θ corresponding to the type of the pattern may be selected. In this case, the intensity of the magnetic field applied to the optical material can be made uniform irrespective of the optical material.

For example, when the template 2 is irradiated with the light having the polarization plane of 45 degrees with respect to the repetitive direction of the repetitive pattern formed in the template 2, a difference between the large defect such as the pattern bridge defect and the broken pattern defect and the small defect such as the edge roughness can emerge in the sensitivity to the electric field component of the light. On the other hand, when the template 2 is irradiated with the light having the polarization plane of 0 degree or 90 degrees with respect to the repetitive direction of the repetitive pattern formed in the template 2, the large defect and the small defect cannot be distinguished from each other because the large defect is equal to the small defect in the light sensitivity. That is, the polarization plane of the light with which the pattern is illuminated is not necessarily 45 degrees with respect to the repetitive direction of the repetitive pattern, but it is necessary that the polarization plane of the light not be 0 degrees or 90 degrees with respect to the repetitive direction of the repetitive pattern. In other words, preferably the polarization plane of the light is set to any angle except an angle within a range of an angle equal to or larger than −5 degrees and an angle equal to or smaller than 5 degrees, and a range of an angle equal to or larger than 85 degrees and an angle equal to or smaller than 95 degrees.

In the present embodiment, preferably the light is transmitted through the Faraday rotator 204 twice, that is, back and forth, to rotate the light polarization plane by 90 degrees. That is, preferably the magnetic field is applied to the optical material such that the light is rotated by 90 degrees while transmitted back and forth.

As illustrated in FIG. 17, linearly polarized light L is transmitted through the half-wavelength plate 203 to rotate the polarization plane of the linearly polarized light L by 45 degrees. Then, the linearly polarized light L is transmitted through the Faraday rotator 204 to further rotate the polarization plane of the linearly polarized light L by 45 degrees. Then, the image of the linearly polarized light L is formed on the template (not illustrated in FIG. 17) through the objective lens 205.

Referring to FIG. 18, the linearly polarized light L reflected by the template (not illustrated in FIG. 18) is transmitted through the objective lens 205, and incident on the Faraday rotator 204. Then, the linearly polarized light L is transmitted through the Faraday rotator 204 to rotate the polarization plane of the linearly polarized light L by 45 degrees. Then, the linearly polarized light L is transmitted through the half-wavelength plate 203 to rotate the polarization plane of the linearly polarized light L by −45 degrees.

Thus, the linearly polarized light L is transmitted through the Faraday rotator 204 twice to rotate the polarization direction of the linearly polarized light L by 90 degrees. Therefore, in FIG. 14, the light emitted from the light source 201 is reflected by the polarization beam splitter 202, and oriented toward the template 2. Because the polarization plane of the light reflected by the template 2 is rotated by 90 degrees, the light is transmitted through the polarization beam splitter 202, and the light is oriented toward the sensor 207, not the light source 201. When the light is incident on the sensor 207, the sensor 207 captures the optical image of the template 2.

The polarization direction of the light with which the template 2 is irradiated is changed by not only the Faraday rotator 204 but also the half-wavelength plate 203. As described above, for the Faraday rotator 204, the polarization direction of the light can be changed by changing the magnetic field applied to the optical material 204a. On the other hand, for the half-wavelength plate 203, the rotation angle can arbitrarily be changed by providing a rotary mechanism in the half-wavelength plate 203. In FIG. 14, the half-wavelength plate 203 may be arranged between the Faraday rotator 204 and the objective lens 205.

The pattern image (of the template 2) captured by the sensor 207 is converted into the optical image data, and used in the inspection. Specifically, the process is as follows.

After the pattern images incident to the sensor 207 are subjected to photoelectric conversion, they are subjected to A/D (Analog to Digital) conversion by the sensor circuit 106 to become the optical image data. After that, the optical image data is sent to the image processing circuit 108.

In the image processing circuit 108, the optical image data is expressed by the gradation value of each pixel. For example, one of values of a 0 gradation value to a 255 gradation value is provided to each pixel using a gray scale having 256-level gradation value.

In the image processing circuit 108, a Faraday rotation angle θ of the Faraday rotator 204 is determined such that the light scattered by the edge roughness in the light reflected from the template 2 is prevented from being incident on the sensor 207 (S4 in FIG. 8). The determined Faraday rotation angle θ is sent to the angle control circuit 14, and the angle control circuit 14 changes a current passed through a coil of the Faraday rotator 204, whereby the magnetic field applied to the optical material is changed to obtain the Faraday rotation angle θ set by the image processing circuit 108. At this point, the optical image of the template 2 is acquired again (S5 in FIG. 8). When the template 2 is irradiated with the light from the light source 201 on the condition that the Faraday rotation angle θ is obtained, the light scattered by the pattern bridge defect or broken pattern defect is incident on the sensor 207 through the half-wavelength plate 203 and the polarization beam splitter 202 while separated from the light scattered by the edge roughness. As a result, in the optical image captured by the sensor 207, the pattern bridge defect and the broken pattern defect are left while unevenness of light and darkness caused by the edge roughness is removed. Accordingly, the use of the optical image can inspect the pattern bridge defect and the broken pattern defect. That is, the pattern finer than the resolution limit of the optical system can be inspected by the above inspection method. In particular, the Faraday rotation angle θ is determined in S4 using the programmed defect formed in the alignment mark, so that the optimum Faraday rotation angle θ can be obtained irrespective of the existence or non-existence of the defect in the pattern to be inspected.

Next, a specific method for finding the condition that removes the bright and dark unevenness caused by the edge roughness as shown in S4 in FIG. 8 will be described.

Generally, there is a large amount of edge roughness existing in the whole surface of the template of the inspection target while very few number of pattern bridge defects or broken pattern defects exist in the template. For example, when the optical image having the region of 100 μm×100 μm is acquired, there is a small possibility that the pattern bridge defect or the broken pattern defect is included in the region, and there are very few defects existing in the region even if the pattern bridge defect or the broken pattern defect is included in the region. That is, almost all the optical images in the region are caused by the edge roughness. This means that the condition that removes the defect caused by the edge roughness is obtained from one optical image having the dimension of approximately 100 μm× approximately 100 μm.

As mentioned above, the change in gradation value caused by the edge roughness in the optical image can be removed by controlling the polarization direction of the light incident to the sensor 207. Specifically, the quantity of light that is incident to the sensor 207, while being scattered by the edge roughness, is changed by controlling the Faraday rotation angle θ using the Faraday rotator 204, which allows the bright and dark amplitude to be changed in the optical image.

The bright and dark amplitude in the optical image is expressed by a standard deviation of the gradation value in each pixel. For example, assuming that the optical system has a pixel resolution of 50 nm in the inspection apparatus 100 in FIG. 14, the optical image having the region of 100 μm×100 μm is expressed by 4 million pixels. That is, a specimen of 4 million gradation values is obtained from the one optical image.

For a dark-field illumination system, the standard deviation is obtained with respect to the specimen, the obtained standard deviation is defined as a degree of the scattering light caused by the edge roughness, and the polarization state on the imaging optical system side, namely, the Faraday rotation angle θ is adjusted such that the standard deviation becomes the minimum. Therefore, the quantity of scattering light incident to the sensor 207 due to the edge roughness can be minimized.

For the optical image in a bright-field optical system, a degree of the brightness and darkness caused by the edge roughness is influenced by zero-order light. The reason is as follows. Because the periodic pattern finer than the optical resolution limit exists in the inspection target, the polarization state of the zero-order light changes due to a phase-difference effect caused by structural birefringence. Therefore, the light quantity that becomes a base also changes when the Faraday rotation angle θ is changed in order to remove the reflected light caused by the edge roughness. Because the bright-field image is a product of an electric field amplitude of the scattering light from the pattern bridge defect, the broken pattern defect, or the edge roughness and an electric field amplitude of the zero-order light, the degree of the brightness and darkness caused by the edge roughness is influenced by an intensity of the zero-order light.

In order to remove the influence of the scattering light due to the edge roughness to improve the detection sensitivity for the pattern bridge defect or broken pattern defect, it is necessary to find, not the condition in which a function (specifically, a function expressing the electric field amplitude of the zero-order light) caused by the zero-order light becomes the minimum, but the condition that a function (specifically, a function expressing the electric field amplitude of the scattering light caused by the edge roughness) caused by the edge roughness becomes the minimum. The reason the function caused by the zero-order light becomes the minimum is that the function caused by the zero-order light is the condition that the base light quantity simply becomes the minimum but the influence of the edge roughness is not completely removed.

The function caused by the edge roughness becoming the minimum is obtained by a calculation using a standard deviation σ of the gradation value of the optical image and an average gradation value A. The standard deviation σ includes various noise factors, and particularly the standard deviation σ is largely influenced by the brightness and darkness caused by the edge roughness. The average gradation value A of the optical image is the base light quantity, namely, the intensity of the zero-order light. The electric field amplitude of the scattering light due to the edge roughness is proportional to a value in which the standard deviation σ of the optical image is divided by a square root of the average gradation value A. In order to find the condition that minimizes the bright and dark amplitude caused by the edge roughness, the optical image is acquired while the Faraday rotation angle θ is changed, and the value ($\sigma/\sqrt{A}$) in which the standard deviation of the gradation value in the obtained optical image is divided by the square root of the average gradation value is calculated. The Faraday rotation angle $\theta$ is obtained when the value ($\sigma/\sqrt{A}$) becomes the minimum.

As mentioned above, for the large defect such as the pattern bridge defect and the broken pattern defect, the vertical direction and the horizontal direction differ from each other in the sensitivity to the electric field component of the illumination light. Accordingly, when the electric field amplitude of the scattering light caused by the large defect becomes the minimum, the Faraday rotation angle $\theta$ differs from that of the scattering light caused by the edge roughness. That is, even if the Faraday rotation angle $\theta$ is applied when the electric field amplitude of the scattering light caused by the edge roughness becomes the minimum, the electric field amplitude of the scattering light caused by the pattern bridge defect or the broken pattern defect does not become the minimum. Therefore, the pattern bridge defect and the broken pattern defect can be detected without being buried in the amplitude of the brightness and darkness caused by the edge roughness.

As described above the Faraday rotation angle $\theta$ that properly separates the light scattered by the pattern bridge defect or the broken pattern defect from the light scattered by the edge roughness depends on the pattern structure. The detail is described as follows.

When the electric field amplitude of the scattering light caused by the edge roughness becomes the minimum, the Faraday rotation angle $\theta$ depends on a structure of the pattern formed in the inspection target. For example, Faraday rotation angle $\theta$ at which the electric field amplitude of scattering light caused by edge roughness becomes the minimum also changes when a pitch of the pattern, a depth of the dugout portion, or a line and space ratio of the pattern changes. Accordingly, it is necessary to obtain the Faraday rotation angle $\theta$ according to the structure of the pattern of the inspection target. In the case that the identical pattern is provided in all inspection targets, the previously obtained Faraday rotation angle $\theta$ can continuously be used in the inspection process. On the other hand, in the case that a plurality of patterns each having a different structure are provided in the inspection target, it is necessary to change the Faraday rotation angle $\theta$ according to the pattern. Additionally, even in the identical design pattern, the depth or the line and space ratio is slightly changed by various error factors, and possibly the Faraday rotation angle $\theta$ that minimizes the electric field amplitude of the scattering light, varies in the inspection target. In this case, it is necessary to follow the variation to change the Faraday rotation angle $\theta$.

Thus, the condition that removes the bright and dark unevenness caused by the edge roughness, namely the Faraday rotation angle $\theta$ can be obtained. This processing is performed prior to the inspection of the template 2. As previously mentioned, this step (S4 in FIG. 8) is performed in the previous stage of the inspection of the template 2 (S5 and S6 in FIG. 8). That is, in order to find the condition that removes the defect caused by the edge roughness, the sensor 207 captures the optical image of the programmed defect of the alignment mark arranged in the template 2 while the Faraday rotation angle $\theta$ is changed. Specifically, the angle control circuit 14 changes the current passed through the coil of the Faraday rotator 204, and thereby the intensity of the magnetic field applied to the optical material is changed such that the predetermined Faraday rotation angle $\theta$ is obtained. For example, one optical image having the dimension of approximately 100 µm× approximately 100 µm may be obtained in each predetermined value of the Faraday rotation angle $\theta$. The generated data of the optical image is sent to the image processing circuit 108 through the sensor circuit 106, and the Faraday rotation angle $\theta$ of the Faraday rotator 204 is set such that the light scattered by the edge roughness in the light from the template 2 is prevented from being incident to the sensor 207.

As described above, the optical image data is expressed by the gradation value of each pixel in the image processing circuit 108. Therefore, in the dark-field illumination system, the standard deviation is obtained with respect to one optical image, the obtained standard deviation is defined as the degree of the scattering light caused by the edge roughness, and the Faraday rotation angle $\theta$ is obtained such that the standard deviation becomes the minimum. On the other hand, in the bright-field illumination system, the optical image is acquired while the Faraday rotation angle $\theta$ is changing, and then calculates a value in which the standard deviation $\sigma$ of the average gradation value in the acquired optical image is divided by the square root of the average gradation value A. The Faraday rotation angle $\theta$ is obtained when the value becomes the minimum.

Information on the Faraday rotation angle $\theta$ obtained by the image processing circuit 108 is sent to the angle control circuit 14. The angle control circuit 14 controls the current passed through the coil of the Faraday rotator 204 according to the information from the image processing circuit 108. Therefore, the intensity of the magnetic field applied to the optical material of the Faraday rotator 204 can be changed to set the Faraday rotation angle $\theta$ to the value obtained by the image processing circuit 108.

The Faraday rotation angle $\theta$ is set to the above value, and the optical image of the pattern, that is a pattern to be inspected on the imprint surface of the template, that is a first pattern (not shown) to be imprinted to the wafer, is acquired (S5 in FIG. 8). The light scattered by the pattern bridge defect or the broken pattern defect is incident to the sensor 207 through the half-wavelength plate 203 and the polarization beamsplitter 202 while separated from the light scattered by the edge roughness because the light scattered by the edge roughness is prevented from being incident to the sensor 207. In the optical image captured by the sensor 207, the pattern bridge defect and the broken pattern defect are left while the light-dark unevenness caused by the edge roughness is removed. Accordingly, the use of the optical image can inspect the pattern bridge defect and the broken pattern defect, namely, the pattern finer than the optical resolution limit.

When the optical image in which the defect caused by the edge roughness is removed, is sent to the image processing circuit 108, the pixel data in the optical image is expressed by the gradation value of each pixel. The inspection area of the template 2 may be divided into predetermined unit regions, the average gradation values for each unit area is determined. Predetermined unit area, for example, can be a 1 mm×1 mm region.

The information on the gradation value obtained by the image processing circuit 108 is sent to the defect detection circuit 134. The defect detection circuit 134 performs a defect determination of the pattern to be inspected in the template 2 (S6 in FIG. 8).

As previously mentioned, when the pattern bridge defect or the broken pattern defect exists in the repetitive pattern finer than the optical resolution limit of the optical system, an irregularity is generated in the regularity of the pattern, the gradation value in the location where the defect exists varies from the surrounding gradation value. Therefore, the pattern bridge defect or the broken pattern defect can be detected. Specifically, the defect detection circuit 134, for example, has thresholds above and below the average gradation value as the center, and the location is recognized as the defect when the gradation value sent from the image processing circuit 108 exceeds the threshold. The threshold level is set in advance of the inspection. For example, the defect information obtained by the defect detection circuit 134 is stored in the magnetic disk device 109.

The inspection apparatus 100 can also have a review function in addition to the inspection function. As used herein, the review means an operation in which an operator determines whether the detected defect will become a problem from a practical point of view.

For example, a coordinate and an optical image of a location determined to be the defect by the defect detection circuit 134 are sent to a review tool (not illustrated). An operator reviews the optical image by comparison with a standard image that is a model image. The defect information determined by the review can be stored as a defect information list in the magnetic disk device 109. As an example, a reference image produced by design data of the inspection target pattern is used as the standard image.

As described above, in the first embodiment, the programmed defect is previously formed in the template, and the focus offset is adjusted using the programmed defect, so that the inspection can be performed while the optimum focus offset is always maintained. Therefore, reliability of the inspection result can be enhanced.

In the first embodiment, the condition that the unevenness of the light and darkness scattered by the edge roughness is removed, namely, the Faraday rotation angle $\theta$ at which the amount of light, which is scattered by the edge roughness and incident on the sensor 207, is minimized is found using the programmed defect formed in the template. Therefore, the pattern finer than the resolution limit of the optical system can accurately be inspected. More particularly, the optical image, in which the unevenness of the light and darkness caused by the edge roughness is removed, is acquired to be able to inspect the pattern bridge defect and the broken pattern defect.

Second Embodiment

In the second embodiment, the alignment mark includes the second pattern that is formed in the inspection region to simulate the first pattern finer than the resolution limit of the optical system, the region, where the second pattern is not arranged and the mark used in the alignment is formed by the contrast with the region where the second pattern is arranged, and the programmed defect formed in the region where the second pattern is formed. An alignment mark of a second embodiment has a configuration similar to that of the first embodiment. However, while the alignment marks are arranged in the four corners of the imprint surface of the template in the first embodiment, the alignment marks of the second embodiment are arranged without limiting to the four corners of the imprint surface.

Figure 31:
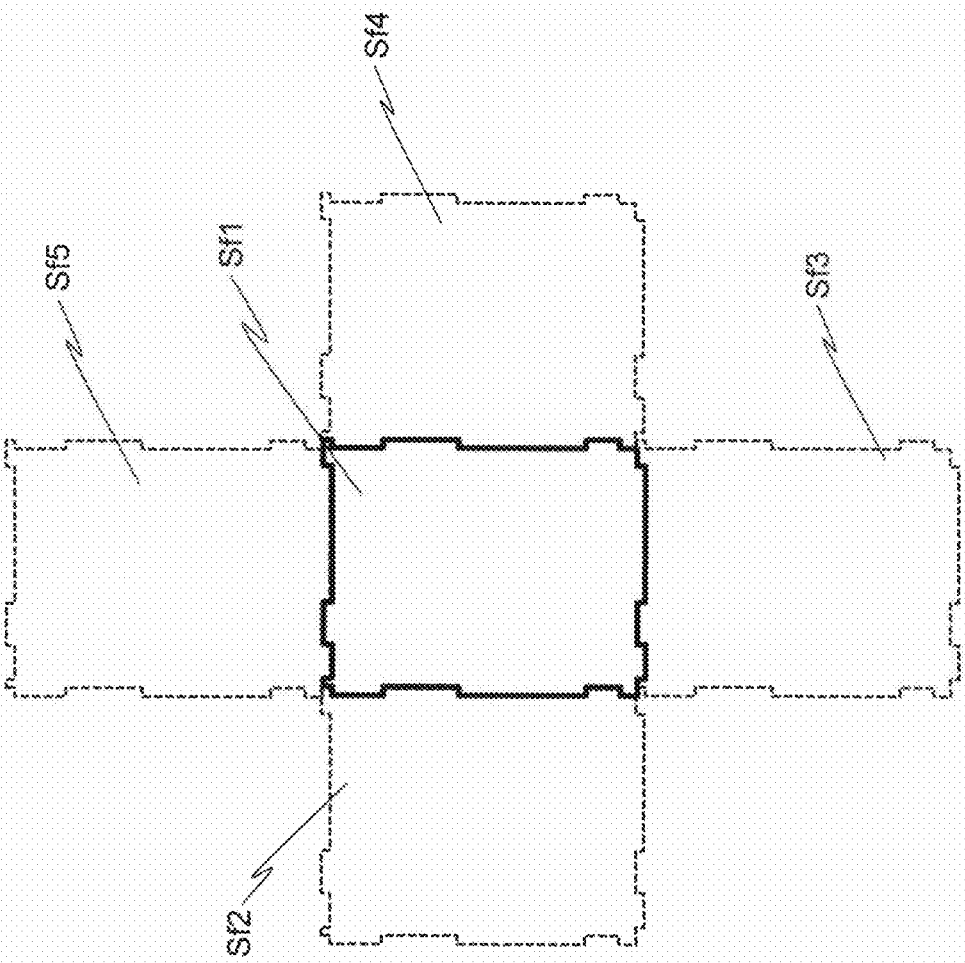
FIG. 31 is a schematic plan view illustrating the imprint surface of the template according to the second embodiment.

FIG. 31 is a schematic plan view illustrating a imprint surface of the template that is imprinted to the wafer through the resist a plurality of times. In FIG. 31, regions (Sf2 to Sf5) indicated by dotted lines are other imprint surfaces that are imprinted to the surroundings of the imprint surface Sf1. As can be seen from FIG. 31, an outline of the imprint surface has a complex irregular shape. This is because the adjacent imprint surfaces are fitted in each other so as not to overlap each other.

Figure 32:
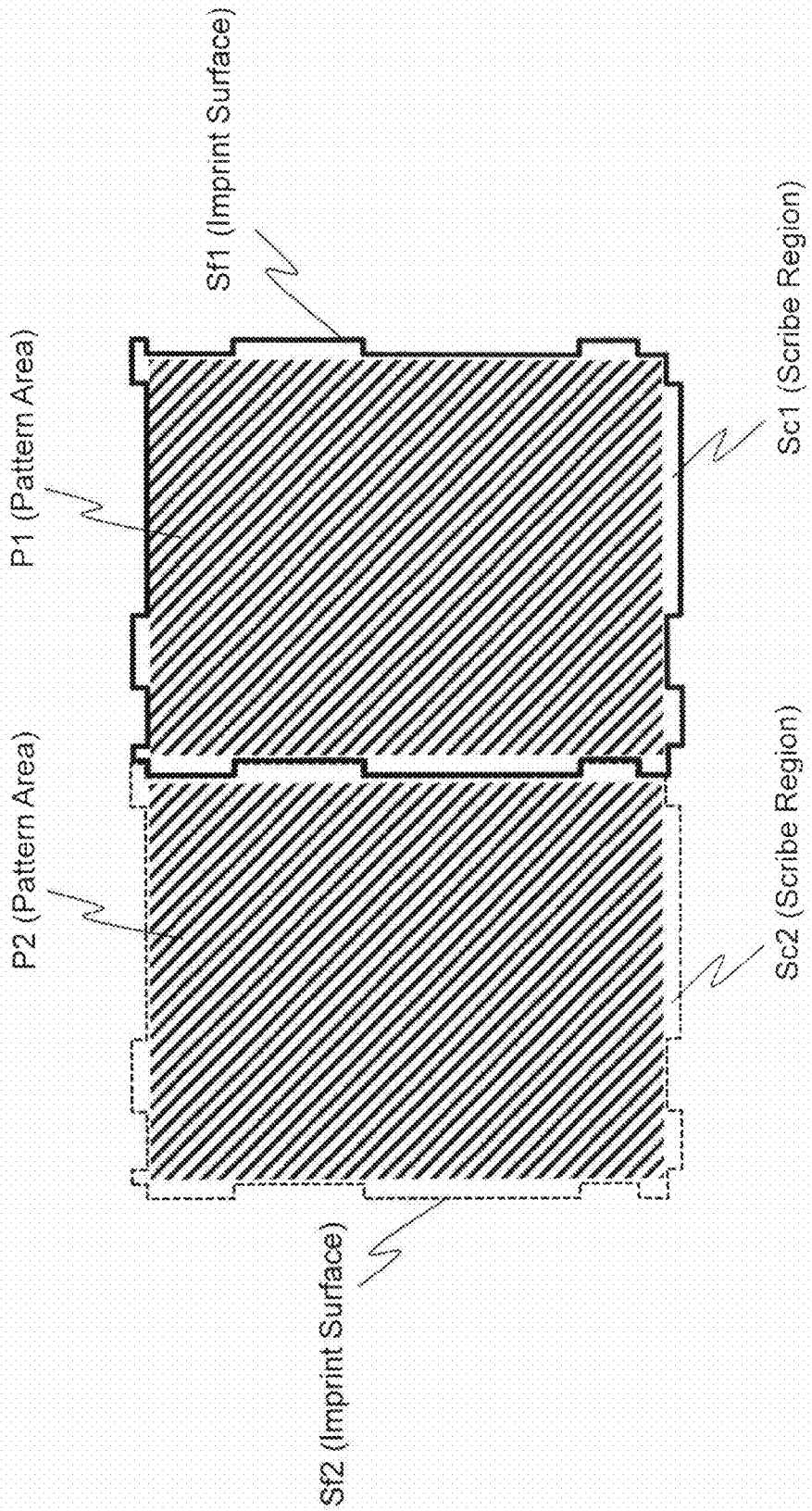
FIG. 32 is an enlarged view of a part of the imprint surface of the template according to the second embodiment.

FIG. 32 is an enlarged view of imprint surfaces Sf1 and Sf2. Diagonal-line portions P1 and P2 are pattern regions where the functional circuit patterns are formed. Regions between the pattern regions P1 and P2 and the outer peripheries of the imprint surfaces Sf1 and Sf2 are scribe regions Sc1 and Sc2 that are used to finally cut the chips although imprinted to the wafer. The scribe regions Sc1 and Sc2 are overlapping margin regions that are provided such that the pattern regions P1 and P2 do not overlap each other during the imprint. For example, the widths of the scribe regions Sc1 and Sc2 range from approximately 50 µm to approximately 100 µm.

The alignment mark is arranged in the scribe region so as not to disturb a layout of the circuit pattern. In the case that the alignment marks are arranged in the four corners of the imprint surface as shown in the first embodiment, the X-coordinate of each alignment mark is matched with one of the X-coordinates of other alignment marks, and the Y-coordinate of each alignment mark is also matched with one of the Y-coordinates of other alignment marks. However, because the outline of the imprint surface has the complex shape, the scribe region also has the complex shape, and it may be difficult to arrange the alignment marks in the four corners of the imprint surface.

For this reason, a plurality of alignment marks are arranged in the scribe region, the X-coordinate of the template pattern is matched with the X-coordinate of the table in the inspection apparatus when the Y-coordinates of two alignment marks are matched with each other, and the Y-coordinate of the template pattern is matched with the Y-coordinate of the table in the inspection apparatus when the X-coordinates of the other two alignment marks are matched with each other. In this case, it is only necessary to arrange the alignment mark in the scribe region, however the region where the alignment mark is arranged is not limited to the four corners of the imprint surface.

Figure 33:
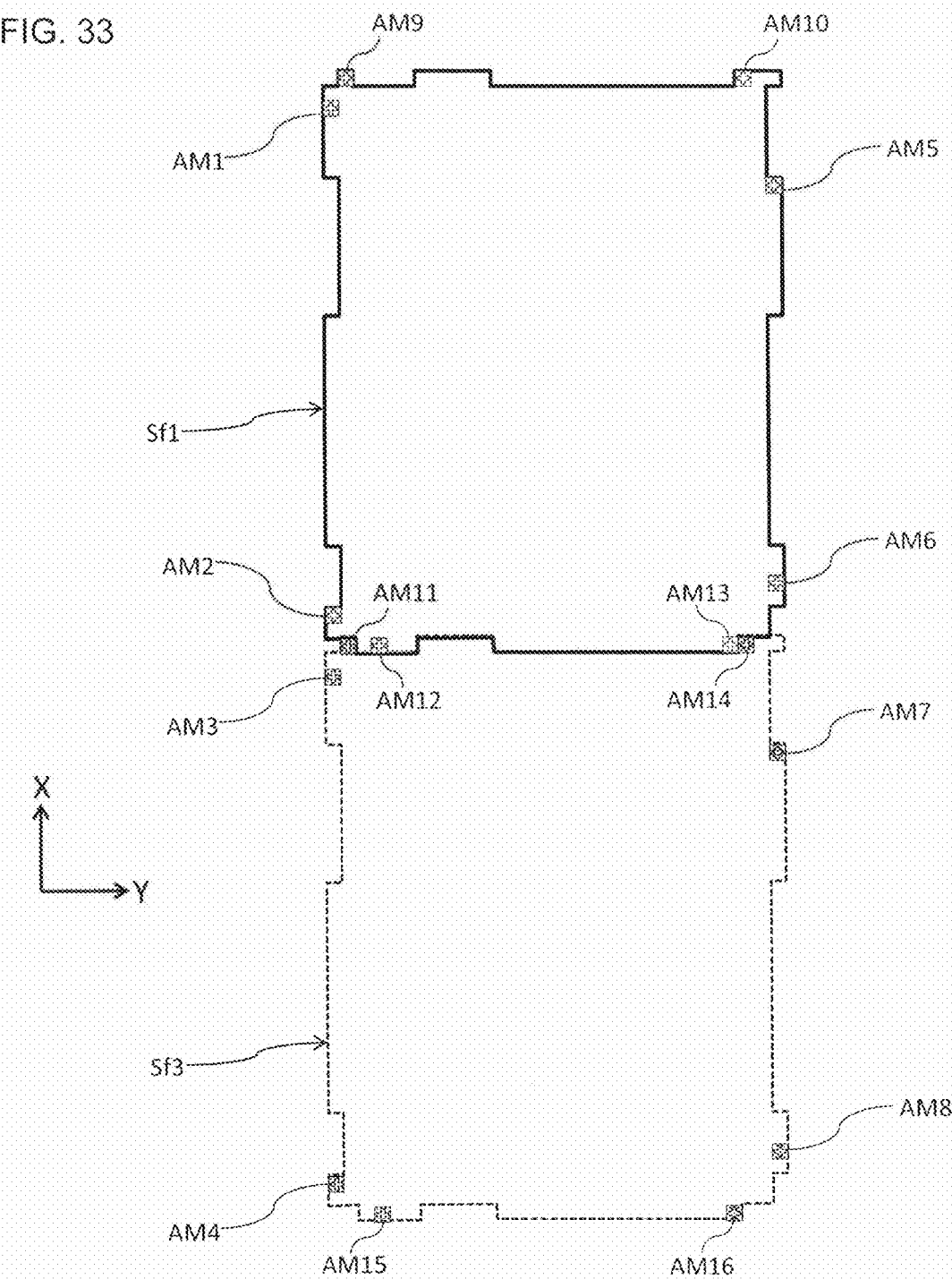
FIG. 33 is an enlarged view of the imprint surface Sf1 and Sf3 shown in FIG. 31.

FIG. 33 is an enlarged view of the imprint surface Sf1 and Sf3 shown in FIG. 31. In FIG. 33, alignment marks AM1, AM2, AM5, AM6, AM9, AM10, AM12, and AM13 are provided in the imprint surface Sf1. On the other hand, alignment marks AM3, AM4, AM7, AM8, AM11, AM14, AM15, and AM16 are provided in the imprint surface Sf3.

For the imprint surface Sf1, the X-coordinate of the template pattern is matched with the X-coordinate of the table in the inspection apparatus when the Y-coordinates of the alignment marks AM1 and AM2 are matched with each other or when the Y-coordinates of the alignment marks AM5 and AM6 are matched with each other. The Y-coordinate of the template pattern is matched with the Y-coordinate of the table in the inspection apparatus when the X-coordinates of the alignment marks AM9 and AM10 are matched with each other or when the X-coordinates of the alignment marks AM12 and AM13 are matched with each other.

For the imprint surface Sf3, the X-coordinate of the template pattern is matched with the X-coordinate of the table in the inspection apparatus when the Y-coordinates of the alignment marks AM3 and AM4 are matched with each other or when the Y-coordinates of the alignment marks AM7 and AM8 are matched with each other. The Y-coordinate of the template pattern is matched with the Y-coordinate of the table in the inspection apparatus when the X-coordinates of the alignment marks AM11 and AM14 are matched with each other or when the X-coordinates of the alignment marks AM15 and AM16 are matched with each other.

The configuration of the alignment mark of the second embodiment is similar to that of the alignment mark of the first embodiment. The inspection method of the second embodiment is similar to that of the first embodiment in FIGS. 8 and 14.

In the second embodiment, the alignment marks are provided without limiting the alignment marks to the four corners of the imprint surface, so that a degree of freedom in design can be enhanced. The focus offset is adjusted using the programmed defect formed in the alignment mark, so that the inspection can be performed while the optimum focus offset is always maintained. As a result, the reliability of the inspection result can be enhanced. The condition in which the unevenness of the light and darkness scattered by the edge roughness is removed, namely, the Faraday rotation angle $\theta$ at which the amount of light, which is scattered by the edge roughness and incident on the sensor, is minimized is found using the programmed defect formed in the alignment mark. Therefore, the pattern finer than the resolution limit of the optical system can accurately be inspected. More particularly, the optical image in which the unevenness of the light and darkness caused by the edge roughness is removed is acquired to be able to inspect the pattern bridge defect and the broken pattern defect.

Third Embodiment

In the first and second embodiments, the programmed defect is formed in the alignment mark. In a third embodiment, the programmed defect is formed in the imprint surface of the template that does not include the alignment mark.

As described in the first embodiment, preferably the alignment marks are arranged in the four corners (or the areas surrounding the four corners) close to the outer periphery of the imprint surface. As described in the second embodiment with reference to FIGS. 31 to 33, the scribe region in the outer periphery of the imprint surface has the complex shape. Accordingly, when the programmed defect is formed in the alignment mark like the first and second embodiments, the scribe region can effectively be used. On the other hand, the programmed defects are not necessarily arranged in the four corners (or the areas surrounding the four corners) close to the outer periphery of the imprint surface. Therefore, in the third embodiment, the design restriction regarding the programmed defect can be relaxed, when the programmed defect is provided in the scribe region while separated from the alignment mark.

Figure 34:
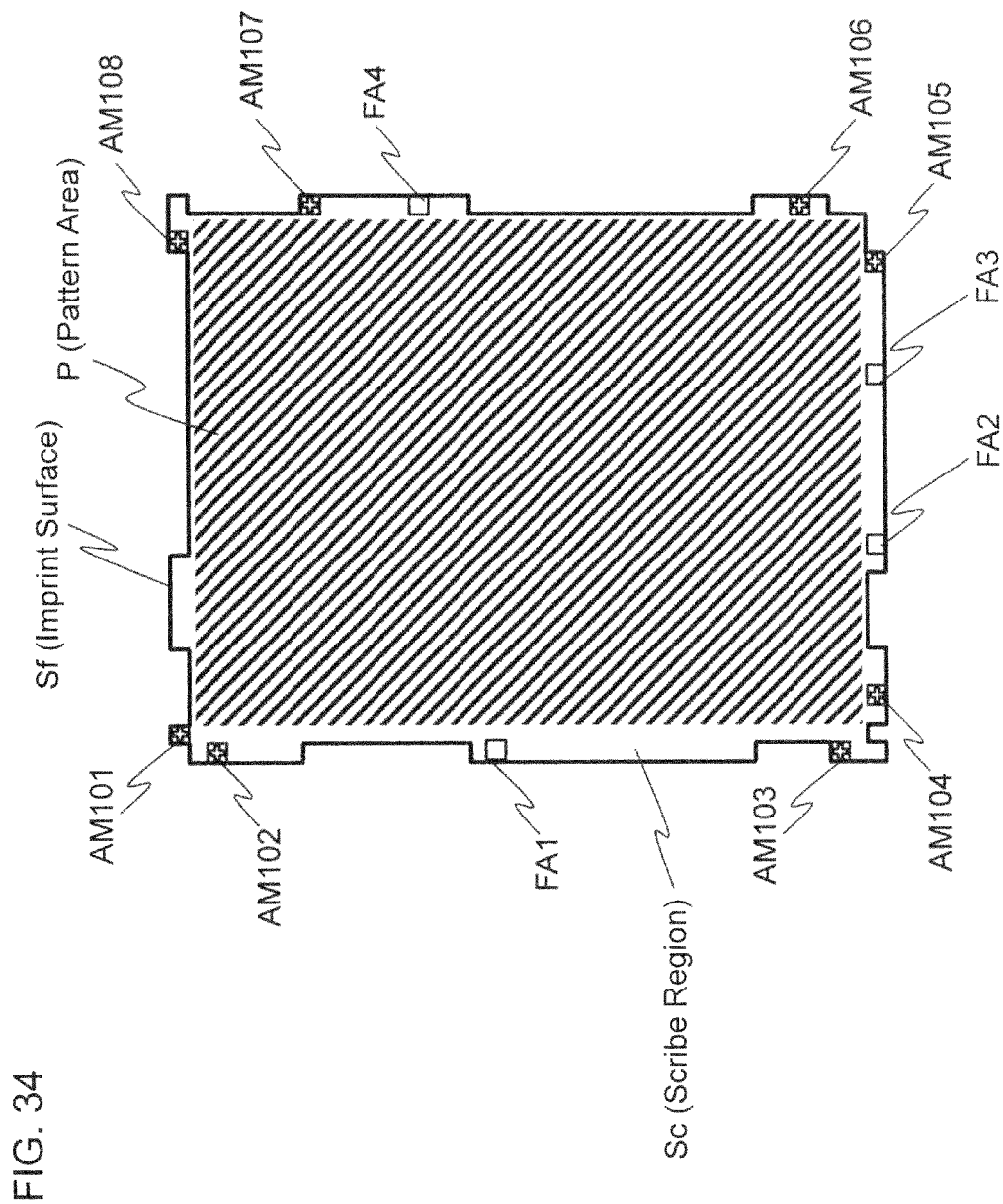
FIG. 34 is a schematic plan view of the imprint surface of the template according to the third embodiment.

FIG. 34 is a schematic plan view of the imprint surface Sf of the template according to the present embodiment.

In FIG. 31, hatched portions P is a pattern region where the circuit pattern is formed, corresponding to the inspection area. In the pattern region P a repeating pattern (not shown), such as a line-and-space pattern, that is, regular pattern repeated with a periodicity is formed. At least a part of the pattern is the pattern (first pattern) finer than the resolution limit of the optical system in the inspection apparatus. Because the first pattern is similar to the first pattern of the first embodiment, a repeated description is omitted.

The region between the pattern region P and an outer edge of the imprint surface Sf is a scribe region Sc. In the third embodiment, alignment marks AM101 to AM108 are arranged in the scribe regions Sc of the four corners (or the surroundings of the four corners) of the imprint surface Sf, and focus offset adjustment regions FA1 to FA4 are arranged independently of the alignment marks AM101 to AM108, and the programmed defects are provided in the focus offset adjustment regions FA1 to FA4. The regions where the focus offset adjustment regions FA1 to FA4 are arranged are not limited to the four corners of the imprint surface or the surroundings of the four corners, but it is only necessary to arrange the focus offset adjustment regions FA1 to FA4 in the scribe regions.

The second patterns that simulate the first pattern, which is formed in the pattern region P and finer than the resolution limit of the optical system, are provided in the focus offset adjustment regions FA1 to FA4. The programmed defect of the mask pattern finer than the resolution limit of the optical system in the inspection apparatus, in other words, the programmed defect that cannot be resolved by the wavelength of the light source in the inspection apparatus is provided in the second pattern. The programmed defect of the first embodiment in FIGS. 19 to 30 can be cited as an example.

In the configuration of the third embodiment, the region where the programmed defect is provided is determined irrespective of the four corners (or the surroundings of the four corners) close to the outer periphery of the imprint surface, so that the degree of freedom in design can be enhanced. As illustrated in FIG. 34, the plurality of focus offset adjustment regions are provided, and the programmed defect is arranged in each focus offset adjustment region. Therefore, for example, even if dirt adheres to the imprint surface Sf thereby not using a part of the focus offset adjustment region in the adjustment of the focus offset, the inspection process can be advanced without problems by the use of other focus offset adjustment region.

The present invention is not limited to the embodiments described and can be implemented in various ways without departing from the spirit of the invention.

In the above embodiments, the programmed defect is provided in the pattern that is of the inspection target provided in the imprint surface of the template, namely, the fine second pattern, which simulates the first pattern imprinted to the wafer and is not able to be resolved by the wavelength of the light source in the inspection apparatus. However, the second pattern does not necessarily simulate the first pattern. In the case that the first pattern differs from the second pattern in the dimension, possibly the optimum value of the focus offset obtained using the programmed defect (the second pattern is used as the background pattern) or the optimum value of the Faraday rotation angle $\theta$ is not matched with the optimum value in the defect of the first pattern. Specifically, in the case that the line width or the distance between the lines varies in the line-and-space pattern, in the case that a hole diameter of the hole pattern or the distance between the holes varies, or in the case that the location of the alignment mark differs from the region to be inspected in a duty ratio defined by a width and a pitch of each line in the line-and-space pattern, the optimum value of the focus offset obtained using the programmed defect or the optimum value of the Faraday rotation angle $\theta$ is not matched with the optimum value in the defect of the first pattern. In such cases, preferably a coefficient used to convert or correct the optimum value of the second pattern into the optimum value of the first pattern is prepared.

In the above embodiments, by way of example, the first pattern and the second pattern are the line-and-space pattern. Alternatively, the first pattern and the second pattern may be a pattern other than the line-and-space pattern, for example, a rectangular pattern. In this case, the pattern bridge defect is the defect in which the rectangles are short-circuited with each other, and the broken pattern defect is the defect in which the rectangle is lacking.

The present invention can also be applied to a substrate other than the template substrate, for example, a mask substrate. In the above embodiments, by way of example, the pattern provided in the template is set to the inspection target, and the alignment mark is provided in the template. In the case that the pattern provided in the mask is set to the inspection target, the alignment mark of the embodiments may be arranged flush with the pattern that is of the inspection target on the mask substrate. Therefore, the defect of the mask pattern finer than the resolution of the optical system in the inspection apparatus can accurately be detected by properly adjusting the focus offset.

In the above embodiments, the "circuit" is also expressed as the "unit". For example, the image processing circuit 108 can also be expressed as an image processor, and the angle control circuit 14 can also be expressed as an angle controller, further the defect detection circuit 134 can also be expressed as a defect detector. These components may be constructed with an electric circuit or by software (program) on a computer. The circuit may also be implemented by not only software but also a combination of hardware and software, or a combination of software and firmware. In the case that the circuit is constructed with software, the software can be recorded in the magnetic disk device 109. For example, each circuit shown in FIG. 5 may be constructed with an electric circuit or software that can be processed by the control computer 110. As another example, each circuit in FIG. 14 may be constructed with a combination of an electric circuit and software. As a more specific example, the defect detection circuit 134, as a defect detector, may be an apparatus construction, or may be implemented as a software program, or may be implemented as a combination of software and firmware, or software and hardware.

The above description of the embodiments has not specified apparatus constructions, control methods, etc., which are not essential to the description of the invention, since any suitable apparatus construction, control methods, etc. can be employed to implement the invention. Further, the scope of this invention encompasses all inspection methods, template substrates, and focus offset methods employing the elements of the invention and variations thereof, which can be designed by those skilled in the art.

What is claimed is:

1. An inspection method for inspecting a substrate to detect a defect using an optical image obtained by irradiating a substrate with light emitted from a light source through an optical system, and causing the light reflected by the substrate to be incident to a sensor through the optical system,
   wherein the substrate includes a first pattern constructed with a repetitive pattern that is not resolved by a wavelength of the light source, and
   at least one alignment mark that is arranged on the same plane as the first pattern,
   wherein the alignment mark includes a second pattern constructed with a repetitive pattern that is not resolved by the wavelength of the light source; and
   a programmed defect that is provided in the second pattern and not resolved by the wavelength of the light source, the inspection method comprising:
   adjusting a focus offset such that a strongest signal of the programmed defect is obtained with respect to a base value of a gradation value in an optical image of the programmed defect by capturing the optical image while changing a focal distance between the surface in which the first pattern is provided and the optical system;
   detecting a defect of the first pattern by capturing an optical image of the first pattern after the focus offset is adjusted.

2. The inspection method according to claim 1, wherein the programmed defect includes a plurality of defects of an identical kind and different size.

3. The inspection method according to claim 2, wherein when signals of the programmed defect having the identical shape and different size change temporally depending on the size, the inspection is stopped without performing the process of detecting a defect of the first pattern by capturing an optical image of the first pattern.

4. The inspection method according to claim 1, wherein the first pattern and the second pattern are a line-and-space pattern or a rectangular pattern, and
   the programmed defect includes at least one of a pattern bridge defect in which lines or rectangles are short-circuited with each other and a broken pattern defect in which the line is disconnected or the rectangle is lacking.

5. The inspection method according to claim 1, wherein the substrate is a template substrate, and the alignment mark includes the second pattern, and a region, where the second pattern is not arranged but a mark used in alignment is formed by contrast with a region where the second pattern is arranged.

6. The inspection method according to claim 1, further comprising optimizing the focus offset obtained from the optical image of the programmed defect provided in the second pattern, in the first pattern when the first pattern differs from the second pattern in size or when the first pattern differs from the second pattern in a duty ratio defined by a width and a pitch of each line while both the first pattern and the second pattern are a line-and-space pattern.

7. The inspection method according to claim 1, wherein the optical system includes a polarization beam splitter, a half-wavelength plate, a Faraday rotator, and an objective lens, further comprising:
   after the focus offset is adjusted, reflecting light emitted from the light source by a polarization beamsplitter, transmitting the light through the half-wavelength plate, the Faraday rotator, the objective lens, irradiating the substrate by the light including a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, capturing an optical image of the programmed defect by causing the light to be incident to the sensor;
   obtaining a gradation value in each pixel with respect to the optical image of the programmed defect, acquiring (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values;
   applying a magnetic field to the Faraday rotator such that the acquired rotation angle is obtained;

capturing an optical image of the first pattern while the magnetic field is applied to the Faraday rotator; and detecting a defect of the first pattern using the optical image of the first pattern;

wherein the first pattern and the second pattern are a line-and-space pattern or a rectangular pattern, and the programmed defect includes at least one of a pattern bridge defect in which lines or rectangles are short-circuited each other and a broken pattern defect in which the line is disconnected or the rectangle is lacking.

8. The inspection method according to claim 7, further comprising optimizing the rotation angle obtained from the optical image of the programmed defect provided in the second pattern, in the first pattern when the first pattern differs from the second pattern in size or when the first pattern differs from the second pattern in a duty ratio defined by a width and a pitch of each line while both the first pattern and the second pattern are the line-and-space pattern.

9. The inspection method according to claim 7, wherein the substrate is a template substrate, and the alignment mark includes the second pattern, and a region, where the second pattern is not arranged but a mark used in alignment is formed by contrast with a region where the second pattern is arranged.

10. The inspection method according to claim 7, wherein when signals of the programmed defect including a plurality of defects having an identical kind and different size, change temporally depending on the size, the inspection is stopped without performing the process of detecting a defect of the first pattern by capturing an optical image of the first pattern.

11. The inspection method according to claim 1, wherein the substrate includes the alignment mark in a scribe region that is arranged at an outer periphery of a region where the first pattern is provided.

12. The inspection method according to claim 11, wherein the alignment marks are arranged in four corners of the substrate.

13. A focus offset method in an inspection method for inspecting a substrate to detect a defect using an optical image obtained by irradiating a substrate with light emitted from a light source through an optical system, and causing the light reflected by the substrate to be incident to a sensor through the optical system, wherein the substrate includes a first pattern constructed with a repetitive pattern that is not resolved by a wavelength of the light source, and at least one alignment mark that is arranged on the same plane as the first pattern, wherein the alignment mark includes a second pattern constructed with a repetitive pattern that is not resolved by the wavelength of the light source, and a programmed defect that is provided in the second pattern and not resolved by the wavelength of the light source, comprising:

adjusting a focus offset such that a strongest signal of the programmed defect is obtained with respect to a base value of a gradation value in an optical image of the programmed defect by capturing the optical image while changing a focal distance between the surface in which the first pattern is provided and the optical system.

\* \* \* \* \*